US010767179B2

(12) United States Patent
Du

(10) Patent No.: US 10,767,179 B2
(45) Date of Patent: Sep. 8, 2020

(54) MICRORNA COMPOSITION FOR THE TREATMENT OF NEUROBLASTOMA

(71) Applicant: Liqin Du, San Antonio, TX (US)

(72) Inventor: Liqin Du, San Antonio, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 16/148,466

(22) Filed: Oct. 1, 2018

(65) Prior Publication Data

US 2019/0062745 A1 Feb. 28, 2019

Related U.S. Application Data

(63) Continuation of application No. 15/118,551, filed as application No. PCT/US2015/015869 on Feb. 13, 2015, now Pat. No. 10,087,444.

(60) Provisional application No. 61/939,730, filed on Feb. 13, 2014.

(51) Int. Cl.
C12N 15/113 (2010.01)
A61K 31/713 (2006.01)
A61K 45/06 (2006.01)

(52) U.S. Cl.
CPC .......... *C12N 15/113* (2013.01); *A61K 31/713* (2013.01); *A61K 45/06* (2013.01); *C12N 2310/141* (2013.01)

(58) Field of Classification Search
CPC ..................... C12N 2310/141; C12N 15/113
See application file for complete search history.

(56) References Cited

U.S. PATENT DOCUMENTS

| | | |
|---|---|---|
| 4,337,063 A | 6/1982 | Mihara et al. |
| 4,404,289 A | 9/1983 | Masuda et al. |
| 4,405,711 A | 9/1983 | Masuda |
| 5,214,136 A | 5/1993 | Lin et al. |
| 5,223,618 A | 6/1993 | Cook et al. |
| 5,268,486 A | 12/1993 | Waggoner et al. |
| 5,378,825 A | 1/1995 | Cook et al. |
| 5,446,137 A | 8/1995 | Maag et al. |
| 5,466,786 A | 11/1995 | Buhr et al. |
| 5,470,967 A | 11/1995 | Huie et al. |
| 5,480,980 A | 1/1996 | Seela |
| 5,602,240 A | 2/1997 | De Mesmaeker et al. |
| 5,610,289 A | 3/1997 | Cook et al. |
| 5,614,617 A | 3/1997 | Cook et al. |
| 5,623,070 A | 4/1997 | Cook et al. |
| 5,637,683 A | 6/1997 | Usher et al. |
| 5,652,099 A | 7/1997 | Conrad |
| 5,670,663 A | 9/1997 | Durzan et al. |
| 5,672,697 A | 9/1997 | Buhr et al. |
| 5,700,922 A | 12/1997 | Cook |
| 5,708,154 A | 1/1998 | Smith et al. |
| 5,714,606 A | 2/1998 | Acevedo et al. |
| 5,728,525 A | 3/1998 | Conrad |
| 5,763,167 A | 6/1998 | Conrad |
| 5,777,092 A | 7/1998 | Cook et al. |
| 5,792,847 A | 8/1998 | Buhr et al. |
| 5,858,988 A | 1/1999 | Wang |
| 5,859,221 A | 1/1999 | Cook et al. |
| 5,872,232 A | 2/1999 | Cook et al. |
| 5,886,165 A | 3/1999 | Kandimalla et al. |
| 6,251,666 B1 | 6/2001 | Beigelman |
| 2006/0185027 A1 | 8/2006 | Bartel et al. |
| 2009/0192111 A1 | 7/2009 | Bader et al. |
| 2010/0021914 A1* | 1/2010 | Moller ............... C12N 15/111 435/5 |
| 2011/0263680 A1 | 10/2011 | Khvorova et al. |
| 2012/0100116 A1 | 4/2012 | Prehaud et al. |
| 2012/0202870 A1 | 8/2012 | Weiner et al. |
| 2013/0225652 A1* | 8/2013 | Chorn ............... C12N 15/111 514/44 A |
| 2013/0331433 A1* | 12/2013 | Thibonnier ......... C12N 15/113 514/44 A |
| 2019/0010491 A1* | 1/2019 | Bentwich .......... C12N 15/111 |

FOREIGN PATENT DOCUMENTS

GB 1529202 10/1978

OTHER PUBLICATIONS

Bentwich et al. Nature Genetics 37, pp. 766-770 (Year: 2005).*
Bentwich et al. Nature Genetics 37, Supplementary Table 1: Novel validated microRNAs (Year: 2005).*
Annibali et al., *PLoS One*, 2012, 7(7):e40269.
Benjamini et al., "Controlling the False Discovery Rate: A Practical and Powerful Approach to Multiple Testing," *Journal of the Royal Statistical Society Series B (Methodological)*, 1995, vol. 57(1), pp. 289-300.
Bier et al., *Oncotarget*, 2013. 4(5):665-76.
Brodeur, "Neuroblastoma: biological insights into a clinical enigma." *Nat Rev Cancer 2003*, vol. 3(3), pp. 203-216.
Chang et al.,*Nat Genet*, 2008, 40(I):43-50.
Cheung et al., "Effects of all-trans-retinoic acid on human SH-SY5Y neuroblastoma as in vitro model in neurotoxicity research." *Neurotoxicology*,2009, vol. 30(1), pp. 127-135.
Conrad and Gerlich. *J Cell Biol*, 2010, 188(4):453-61.
Cruz and Matushansky, *Oncotarget*, 2012, 3(5):559-67.
Foley et al., *Cell Death Differ*, 2011. 18(7):1089-98.
Huang, et al., "Silencing of miR-124 induces neuroblastoma SK-N-SH cell differentiation, cell cycle arrest and apoptosis through promoting AHR." FEBS Letters. vol. 585, pp. 3582-3586, 2011.
International Preliminary Report on Patentability in International Application No. PCT/US2015/015869 dated Aug. 25, 2016.
International Search Report and Written Opinion in International Application No. PCT/US2015/015869 dated May 29, 2015.

(Continued)

*Primary Examiner* — Brian Whiteman
(74) *Attorney, Agent, or Firm* — Norton Rose Fulbright US LLP

(57) ABSTRACT

Certain embodiments are directed to methods of identifying neuroblastoma differentiation-inducing compounds or agent and their use in treating neuroblastoma.

3 Claims, 19 Drawing Sheets
Specification includes a Sequence Listing.

(56) References Cited

OTHER PUBLICATIONS

Jan et al., "High-content screening as a universal tool for fingerprinting of cytotoxicity of nanoparticles." *ACS Nano*, 2008, 2(5), pp. 928-938.
Kinoshita et al., *Oncotarget*, 2012, 3(11):1386-1400.
Kopp et al., "De-targeting by miR-143 decreases unwanted transgene expression in non-tumorigenic cells." *Oncotarget* 2013, vol. 20, pp. 1104-1109.
Kota et al., *Cell*, 2009, 137(6): 1005-17.
Krek et al., "Combinatorial microRNA target predictions." *Nat Genet*, 2005, vol. 37(5), pp. 495-500.
Krutzfeldt et al., "Silencing of microRNAs in vivo with 'antagomirs'." *Nature*, 2005, vol. 438(7068), pp. 685-689.
Laurent et al., "Comprehensive microRNA profiling reveals a unique human embryonic stem cell signature dominated by a single seed sequence." *Stem Cells*, 2008, vol. 26(6). pp. 1506-1516.
Le et al., *Mol Cell Biol*, 2009, 29(19):5290-305.
Lewis et al., *Cell*, 2005, 120(1)15-20.
Li et al., *Aaps J*, 2010, 12(3):309-17.
Liang et al., *BMC Genomics*, 2007, 8:166.
Lin et al., *Cancer Res*, 2010, 70(20):7841-50.
Makeyev et al., *Mol Cell*, 2007, 27(3):435-48.
Mao et al., *Cancer Res*, 2011, 71(12):4314-24.
Maris, et al., "Neuroblastoma" Lance. 369:2106-20, 2007.
Matthay et al., "Treatment of high-risk neuroblastoma with intensive chemotherapy, radiotherapy, autologous bone marrow transplantation, and 13-cis-retinoic acid. Children's Cancer Group." *N Engl J Med*, 1999, vol. 341(16), pp. 1165-1173.
Matthay et al. *J Clin Oncol*, 2009, 27(7):1007-13.
Mishra et al., *J Clin Invest*, 2009, 119(8):2119-23.
Mitchell et al., "A quantitative method for analysis of in vitro neurite outgrowth." *J Neurosci Methods*, 2007, vol. 164(2), pp. 350-362.
Nowak et al., *Blood*, 2009, 113(16):3655-65.
Pahlman, et al., "Phenotypic changes of human neuroblastoma cells in culture induced by 12-O-tratradecanoyl-phorbol-13-acetate" Int J Cancer. 28:583-589, 1981.
Park et al., "Neuroblastoma: biology, prognosis, and treatment." *Hematol Oncol Clin North Am*, 2010, vol. 24(1), pp. 65-86.
Prasad et al., "Role of cyclic AMP in differentiation of human neuroblastoma cells in culture." *Cancer*, 1975, vol. 36(4), pp. 1338-1343.
Price et al., "A simple, flexible, nonfluorescent systemfor the automated screening of neurite outgrowth." *J Biomol Screen*, 2006, vol. 11(2), pp. 155-164.
Radio et al., "Assessment of chemical effects on neurite outgrowth in PC12 cells using high content screening." *Toxicol Sci*, 2008, vol. 105(1), pp. 106-118.
Reynolds and Perez-Polo, "Induction of neurite outgrowth in the IMR-32 human neuroblastoma cell line by nerve growth factor" J Neurosci Res. 6:319-25, 1981.
Reynolds, "Differentiating agents in pediatric malignancies: retinoids in neuroblastoma." Curr Oncol Rep 2000, vol. 2(6), pp. 511-518.
Shenouda et al., "MicroRNA function in cancer: oncogene or a tumor suppressor?" *Cancer Metastasis Rev*, 2009, vol. 28(3-4), pp. 369-378.
Silber et al., *BMC Med*, 2008, 6:14.
Smith et al., *PLoS One*, 2010, 5(6):e11109.
Stark et al., "Animal MicroRNAs confer robustness to gene eression and have a significant impact on 3'UTR evolution." *Cell*, 2005, vol. 123(6), pp. 1133-1146.
Swarbrick et al., *Nat Med*, 2010. 16(10):1134-40.
Thiele et. al., "Decreased expression of N-myc precedes retinoic acid-induced morphological differentiation of human neuroblastoma." *Nature*, 1985, vol. 313(6001), pp. 404-406.
Tivnan et al., *BMC Cancer*, 2011, 11:33.
Trang et al., *Mol Ther*, 2011, 19(6):1116-22.
Wei et al., *Oncogene*, 2008, 27(39):5204-13.
Yeyeodu et al. *Curr Chem Genomics*, 2010, 4:74-83.

\* cited by examiner

SEQUENCE LISTING

<160> NUMBER OF SEQ ID NOS: 21

<210> SEQ ID NO 1
<211> LENGTH: 21
<212> TYPE: RNA
<213> ORGANISM: Artificial Sequence
<220> FEATURE:
<223> OTHER INFORMATION: Synthetic Primer

<400> SEQUENCE: 1
uaaggcaccc uucugaguag a                                              21

<210> SEQ ID NO 2
<211> LENGTH: 20
<212> TYPE: RNA
<213> ORGANISM: Artificial Sequence
<220> FEATURE:
<223> OTHER INFORMATION: Synthetic Primer

```
<400> SEQUENCE: 2
uaaggcacgc ggugaaugcc                                              20

<210> SEQ ID NO 3
<211> LENGTH: 7
<212> TYPE: DNA
<213> ORGANISM: Artificial Sequence
<220> FEATURE:
<223> OTHER INFORMATION: Synthetic Primer

<400> SEQUENCE: 3 aaggcac                                                             7

<210> SEQ ID NO 4
<211> LENGTH: 7
<212> TYPE: RNA
<213> ORGANISM: Artificial Sequence
<220> FEATURE:
<223> OTHER INFORMATION: Synthetic Primer

<400> SEQUENCE: 4 gugccuu                                                             7

<210> SEQ ID NO 5
<211> LENGTH: 7
<212> TYPE: RNA
<213> ORGANISM: Artificial Sequence
<220> FEATURE:
<223> OTHER INFORMATION: Synthetic Primer

<400> SEQUENCE: 5 cacgguu                                                             7

<210> SEQ ID NO 6
<211> LENGTH: 23
<212> TYPE: RNA
<213> ORGANISM: Artificial Sequence
<220> FEATURE:
<223> OTHER INFORMATION: Synthetic Primer

<400> SEQUENCE: 6
uauggcuuuu cauuccuaug uga                                          23

<210> SEQ ID NO 7
<211> LENGTH: 22
<212> TYPE: RNA
<213> ORGANISM: Artificial Sequence
<220> FEATURE:
<223> OTHER INFORMATION: Synthetic Primer

<400> SEQUENCE: 7
uggcaguguc uuagcugguu gu                                           22

<210> SEQ ID NO 8
<211> LENGTH: 23
<212> TYPE: RNA
<213> ORGANISM: Artificial Sequence
<220> FEATURE:
<223> OTHER INFORMATION: Synthetic Primer

<400> SEQUENCE: 8
agcagcauug uacagggcua uga                                          23

<210> SEQ ID NO 9
<211> LENGTH: 22
```

```
<212> TYPE: RNA
<213> ORGANISM: Artificial Sequence
<220> FEATURE:
<223> OTHER INFORMATION: Synthetic Primer

<400> SEQUENCE: 9
uugggaucau uuugcaucca ua                                              22

<210> SEQ ID NO 10
<211> LENGTH: 22
<212> TYPE: RNA
<213> ORGANISM: Artificial Sequence
<220> FEATURE:
<223> OTHER INFORMATION: Synthetic Primer

<400> SEQUENCE: 10
uggcagugua uuguuagcug gu                                              22

<210> SEQ ID NO 11
<211> LENGTH: 22
<212> TYPE: RNA
<213> ORGANISM: Artificial Sequence
<220> FEATURE:
<223> OTHER INFORMATION: Synthetic Primer

<400> SEQUENCE: 11
uuggggaaac ggccgcugag ug                                              22

<210> SEQ ID NO 12
<211> LENGTH: 23
<212> TYPE: RNA
<213> ORGANISM: Artificial Sequence
<220> FEATURE:
<223> OTHER INFORMATION: Synthetic Primer

<400> SEQUENCE: 12
uaggcagugu cauuagcuga uug                                             23

<210> SEQ ID NO 13
<211> LENGTH: 23
<212> TYPE: RNA
<213> ORGANISM: Artificial Sequence
<220> FEATURE:
<223> OTHER INFORMATION: Synthetic Primer

<400> SEQUENCE: 13
agcagcauug uacagggcua uca                                             23

<210> SEQ ID NO 14
<211> LENGTH: 22
<212> TYPE: RNA
<213> ORGANISM: Artificial Sequence
<220> FEATURE:
<223> OTHER INFORMATION: Synthetic Primer

<400> SEQUENCE: 14
gaaggcagca gugcuccccu gu                                              22

<210> SEQ ID NO 15
<211> LENGTH: 22
<212> TYPE: RNA
<213> ORGANISM: Artificial Sequence
<220> FEATURE:
<223> OTHER INFORMATION: Synthetic Primer

<400> SEQUENCE: 15
```

```
aggcagugua uuguuagcug gc                                              22

<210> SEQ ID NO 16
<211> LENGTH: 23
<212> TYPE: RNA
<213> ORGANISM: Artificial Sequence
<220> FEATURE:
<223> OTHER INFORMATION: Synthetic Primer

<400> SEQUENCE: 16
uuauugcuua agaauacgcg uag                                             23

<210> SEQ ID NO 17
<211> LENGTH: 23
<212> TYPE: RNA
<213> ORGANISM: Artificial Sequence
<220> FEATURE:
<223> OTHER INFORMATION: Synthetic Primer

<400> SEQUENCE: 17
acaggcggcu guagcaaugg ggg                                             23

<210> SEQ ID NO 18
<211> LENGTH: 21
<212> TYPE: RNA
<213> ORGANISM: Artificial Sequence
<220> FEATURE:
<223> OTHER INFORMATION: Synthetic Primer

<400> SEQUENCE: 18
agagauuacu uugcugccuu a                                               21

<210> SEQ ID NO 19
<211> LENGTH: 21
<212> TYPE: RNA
<213> ORGANISM: Artificial Sequence
<220> FEATURE:
<223> OTHER INFORMATION: Synthetic Primer

<400> SEQUENCE: 19
guuguuucug ugggugccuu a                                               21

<210> SEQ ID NO 20
<211> LENGTH: 20
<212> TYPE: RNA
<213> ORGANISM: Artificial Sequence
<220> FEATURE:
<223> OTHER INFORMATION: Synthetic Primer

<400> SEQUENCE: 20
cagauuacuu ugcugccuua                                                 20

<210> SEQ ID NO 21
<211> LENGTH: 20
<212> TYPE: RNA
<213> ORGANISM: Artificial Sequence
<220> FEATURE:
<223> OTHER INFORMATION: Synthetic Primer

<400> SEQUENCE: 21
uuguuucugu gggugccuua                                                 20
```

MICRORNA COMPOSITION FOR THE TREATMENT OF NEUROBLASTOMA

This application is a continuation application of U.S. Non-Provisional patent application Ser. No. 15/118,551, which is a national phase application under 35 U.S.C. § 371 of International Application No. PCT/US2015/015869, filed Feb. 13, 2015 which claims priority to U.S. Provisional Patent Application Ser. No. 61/939,730 filed Feb. 13, 2014, each of which is incorporated herein by reference in its entirety.

The invention was made with government support under grant number W81XWH-13-1-0241 awarded by Department of Defense. The government has certain rights in the invention.

BACKGROUND

Neuroblastoma is the most common solid tumor of infancy and the most common extracranial solid tumor of childhood, accounting for more than 7% of childhood cancers and 15% of cancer-related childhood deaths (Maris et al., *Lancet*, 2007, 369(9579):2106-20; Park et al., *Hematol Oncol Clin North Am*, 2010, 24(1):65-86). Neuroblastoma arises from the neural crest cell precursors of the sympathetic nervous system that fail to differentiate (Park et al., *Hematol Oncol Clin North Am*, 2010, 24(1):65-86; Brodeur, *Nat Rev Cancer*, 2003, 3(3):203-16)—this provides the basis for differentiation therapy, an approach to induce malignant cells to differentiate into mature cells, thereby leading to cell growth arrest and apoptosis (Park et al., *Hematol Oncol Clin North Am*, 2010, 24(1):65-86; Reynolds, Curr Oncol Rep 2000, 2(6):511-18; Cruz and Matushansky, *Oncotarget*, 2012, 3(5):559-67; Nowak et al., *Blood*, 2009, 113(16): 3655-65). However, only a limited number of differentiation agents have been successfully used to treat neuroblastoma. The differentiation agent 13-cis-retinoic acid (RA) is currently the standard of care for post-remission maintenance therapy in high-risk neuroblastoma (Park et al., *Hematol Oncol Clin North Am*, 2010, 24(1):65-86). Although such treatment has resulted in a significant increase in patient survival, more than 50% of the treated patients still develop recurrence (Matthay et al., *J. Clin Oncol*, 2009, 27(7):1007-13; Matthay et al., *N Engl J Med*, 1999, 341(16):1165-73). Such poor outcomes demand the development of new differentiation agents. Unfortunately, the mechanisms that result in the loss of differentiation ability of neuroblastoma cells are poorly understood, which poses an obstacle to such development. Therefore, identifying additional differentiation agents largely relies on the discovery of new targetable biological molecules that play critical roles in neuroblastoma differentiation.

High-throughput screening approaches significantly facilitate the discovery of novel anti-cancer drugs and drug targets. More recently, high-content screens (HCSs) based on automated cell imaging have been developed. However, current HCSs generally either use genetic engineered cell lines expressing fluorescent signals or involve staining of fixed cells (Conrad and Gerlich, *J Cell Biol*, 2010, 188(4): 453-61; Jan et al., *ACS Nano*, 2008, 2(5):928-38), which are generally time-consuming and consequently limit their broad applications to drug discoveries.

miRNAs are endogenously expressed small RNAs that play a critical role in tumorigenesis (Shenouda and Alahari, *Cancer Metastasis Rev*, 2009, 28(3-4):369-78; Li et al., *Aaps J*, 2010, 12(3):309-17; Kinoshita et al., *Oncotarget*, 2012, 3(11):1386-1400; Kopp and Roidl, *Oncotarget* 2013; Bier et al., *Oncotarget*, 2013, 4(5):665-76). The therapeutic potential of either exogenously increasing cellular miRNAs levels with synthetic miRNA mimics, or inactivating endogenous miRNAs with synthetic miRNA inhibitors has been demonstrated in previous studies (Kota et al., *Cell*, 2009, 137 (6):1005-17; Krutzfeldt et al., *Nature*, 2005, 438(7068):685-89; Trang et al., *Mol Ther*, 2011, 19(6):1116-22). The role of miRNAs in neuroblastoma differentiation and tumorigenesis has been implicated (Lin et al., *Cancer Res*, 2010, 70(20): 7841-50; Chang et al., *Nat Genet*, 2008, 40(1):43-50; Wei et al., *Oncogene*, 2008, 27(39):5204-13; Tivnan et al., *BMC Cancer*, 2011, 11:33; Makeyev et al., *Mol Cell*, 2007, 27(3):435-48; Annibali et al., *PLoS One*, 2012, 7(7):e40269; Le et al., *Mol Cell Biol*, 2009, 29(19):5290-305; Foley et al., *Cell Death Differ*, 2011, 18(7):1089-98; Swarbrick et al., *Nat Med*, 2010, 16(10):1134-40), which suggests the potential of developing novel miRNA-targeting approaches to neuroblastoma differentiation therapy (Mishra and Merlino, *J Clin Invest*, 2009, 119(8):2119-23), and warrants a comprehensive understanding of the involvement of miRNAs in neuroblastoma cell differentiation. However, there has been no concerted effort to comprehensively investigate the functions of the miRNA species in neuroblastoma differentiation.

SUMMARY

Neuroblastoma, the most common extracranial solid tumor of childhood, arises from neural crest cell precursors that fail to differentiate. Inducing cell differentiation is an important therapeutic strategy for neuroblastoma. Embodiments are directed to a direct functional high-content screen to identify differentiation-inducing microRNAs.

Other embodiments are directed to a microRNA-based differentiation therapy for neuroblastoma. MicroRNAs have been discovered that induce neuroblastoma cell differentiation. In certain aspects the differentiation-inducing microRNAs are based from three microRNA seed families. In certain aspects a therapeutic miRNA is a recombinant miRNA mimic and explicitly excludes a naturally occurring miRNA. The seed has been defined as nucleotides 2-8 of a miRNA. Based on the examples studied to date, a large fraction of targets contain in their 3' UTRs perfect Watson-Crick complementary sites to the seed of the miRNA. While this is not a universal rule, it is one of the best features that describes miRNA targets. There are other features, such as low GC content around the seed, and the preferential positioning of the target site towards the edges of the 3'UTRs. Certain microRNA seed families are overrepresented in an identified group of fourteen differentiation-inducing microRNAs, suggesting that microRNA seed families may be functionally relevant in neuroblastoma differentiation. In certain aspects the differentiation-inducing microRNA is a member of the microRNA-506-3p/microRNA-124-3p seed family. The differentiation-inducing function of microRNA-506-3p/microRNA-124-3p is mediated, at least partially, by down-regulating expression of their targets CDK4 and STAT3. The expression of miR-506-3p (mature sequence=uaaggcacccuucugaguaga (SEQ ID NO:1)), but not miR-124-3p (mature sequence=uaaggcacgcggugaaugcc (SEQ ID NO:2)), is dramatically upregulated in differentiated neuroblastoma cells, suggesting the important role of endogenous miR-506-3p in differentiation and tumorigenesis. The functional screen on microRNAs provided a comprehensive analysis of the involvement of microRNA species in neuroblastoma cell differentiation and identified novel differentiation-inducing microRNAs.

Certain embodiments are directed to non-fluorescent, live-cell based high content screen (HCS) method for identifying neuroblastoma differentiation-inducing agents. Neurite outgrowth, which is easily detectable under the microscope, is a well-recognized morphological differentiation marker of neuroblastoma cells in vitro (Thiele et al., *Nature*, 1985, 313(6001):404-06; Pahlman et al., *Int J Cancer*, 1981, 28(5):583-89; Reynolds and Perez-Polo, *J Neurosci Res*, 1981, 6(3):319-25; Prasad and Kumar, *Cancer*, 1975, 36(4): 1338-43). While undifferentiated cells usually show no visible neurites, fully differentiated neuroblastoma cells form neurites that are four to five times the length of the cell body. This differentiation trait facilitates the design of a functional HCS assay to directly identify substances that induce neuroblastoma cell differentiation.

Certain embodiments are directed to a screen for microRNAs (miRNAs) that induce differentiation. By applying the HCS new differentiation-inducing miRNAs were discovered.

In certain aspects a miRNA mimic comprises a seed sequence of aaggcac (SEQ ID NO:3). In a further aspect a neuroblastoma differentiation-inducing miRNA is miR-506-3p or an miRNA mimic comprising the mature sequence thereof.

The term "microRNA" or "miRNA" is used according to its ordinary and plain meaning and refers to a microRNA molecule found in eukaryotes that is involved in RNA-based gene regulation. See, e.g., Carrington et al., 2003, which is hereby incorporated by reference. The term will be used to refer to the single-stranded RNA molecule processed from a precursor. Individual miRNAs have been identified and sequenced in different organisms, and they have been given names. Names of miRNAs and their sequences are provided herein. Additionally, other miRNAs are known to those of skill in the art and can be readily implemented in embodiments of the invention. The methods and compositions should not be limited to miRNAs identified in the application, as they are provided as examples, not necessarily as limitations of the invention.

The present invention concerns, in some embodiments, short nucleic acid molecules that function as miRNAs (i.e., mimics) in a cell. The term "short" refers to a length of a single polynucleotide that is 150 nucleotides or fewer. The nucleic acid molecules are synthetic. The term "synthetic" means the nucleic acid molecule is isolated and not identical in sequence (the entire sequence) and/or chemical structure to a naturally-occurring nucleic acid molecule, such as an endogenous precursor miRNA molecule. While in some embodiments, nucleic acids of the invention do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA.

The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together.

Of course, it is understood that a "synthetic nucleic acid" of the invention means that the nucleic acid does not have a chemical structure or sequence of a naturally occurring nucleic acid. Consequently, it will be understood that the term "synthetic miRNA" refers to a "synthetic nucleic acid" that functions in a cell or under physiological conditions as a naturally occurring miRNA.

While many of the embodiments of the invention involve synthetic miRNAs or synthetic nucleic acids, in some embodiments of the invention, the nucleic acid molecule(s) need not be "synthetic." In certain embodiments, a non-synthetic miRNA employed in methods and compositions of the invention may have the entire sequence and structure of a naturally occurring miRNA precursor or the mature miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA and not a non-synthetic miRNA (that is, not an miRNA that qualifies as "synthetic"); though in other embodiments, the invention specifically involves a non-synthetic miRNA and not a synthetic miRNA. Any embodiments discussed with respect to the use of synthetic miRNAs can be applied with respect to non-synthetic miRNAs, and vice versa.

It will be understood that the term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided; the endogenous miRNA will be referred to as the "corresponding miRNA." Corresponding miRNA sequences that can be used in the context of the invention include, but are not limited to, miR-506-3p or seed family members of the miR-506-3p/miR-124-3p family as well as any other miRNA sequence, miRNA precursor sequence, or any sequence complementary thereof. In some embodiments, the sequence is or is derived from a probe sequence identified in the appendix to target the particular miRNA (or set of miRNAs) that can be used with that probe sequence.

In some embodiments, there is a synthetic miRNA having a length of between 17 and 130 residues. The present invention concerns synthetic miRNA molecules that are, are at least, or are at most 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 residues in length, or any range derivable therein.

In certain embodiments, synthetic miRNA have (a) an "miRNA region" whose sequence from 5' to 3' is identical to a mature miRNA sequence, and (b) a "complementary region" whose sequence from 5' to 3' is between 60% and 100% complementary to the miRNA sequence. In certain embodiments, these synthetic miRNA are also isolated, as defined above.

The term "miRNA region" refers to a region on the synthetic miRNA that is at least 90% identical to the entire sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA.

The term "complementary region" refers to a region of a synthetic miRNA that is or is at least 60% complementary to the mature, naturally occurring miRNA sequence that the miRNA region is identical to. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there is a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

The term "effective amount" means an amount effective, at dosages and for periods of time necessary, to achieve the desired therapeutic or prophylactic result.

An "effective amount" of an anti-cancer agent in reference to decreasing cancer cell growth, means an amount capable of decreasing, to some extent, the growth of some cancer or tumor cells. The term includes an amount capable of invoking a growth inhibitory, cytostatic and/or cytotoxic effect and/or apoptosis of the cancer or tumor cells.

A "therapeutically effective amount" in reference to the treatment of cancer, means an amount capable of invoking one or more of the following effects: (1) inhibition, to some extent, of cancer or tumor growth, including slowing down growth or complete growth arrest; (2) reduction in the number of cancer or tumor cells; (3) reduction in tumor size; (4) inhibition (i.e., reduction, slowing down, or complete stopping) of cancer or tumor cell infiltration into peripheral organs; (5) inhibition (i.e., reduction, slowing down, or complete stopping) of metastasis; (6) enhancement of anti-tumor immune response, which may, but is not required to, result in the regression or rejection of the tumor, or (7) relief, to some extent, of one or more symptoms associated with the cancer or tumor. The therapeutically effective amount may vary according to factors such as the disease state, age, sex and weight of the individual and the ability of one or more anti-cancer agents to elicit a desired response in the individual. A "therapeutically effective amount" is also one in which any toxic or detrimental effects are outweighed by the therapeutically beneficial effects.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

The terms "inhibiting," "reducing," or "prevention," or any variation of these terms, when used in the claims and/or the specification includes any measurable decrease or complete inhibition to achieve a desired result.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figures 1A, 1B:
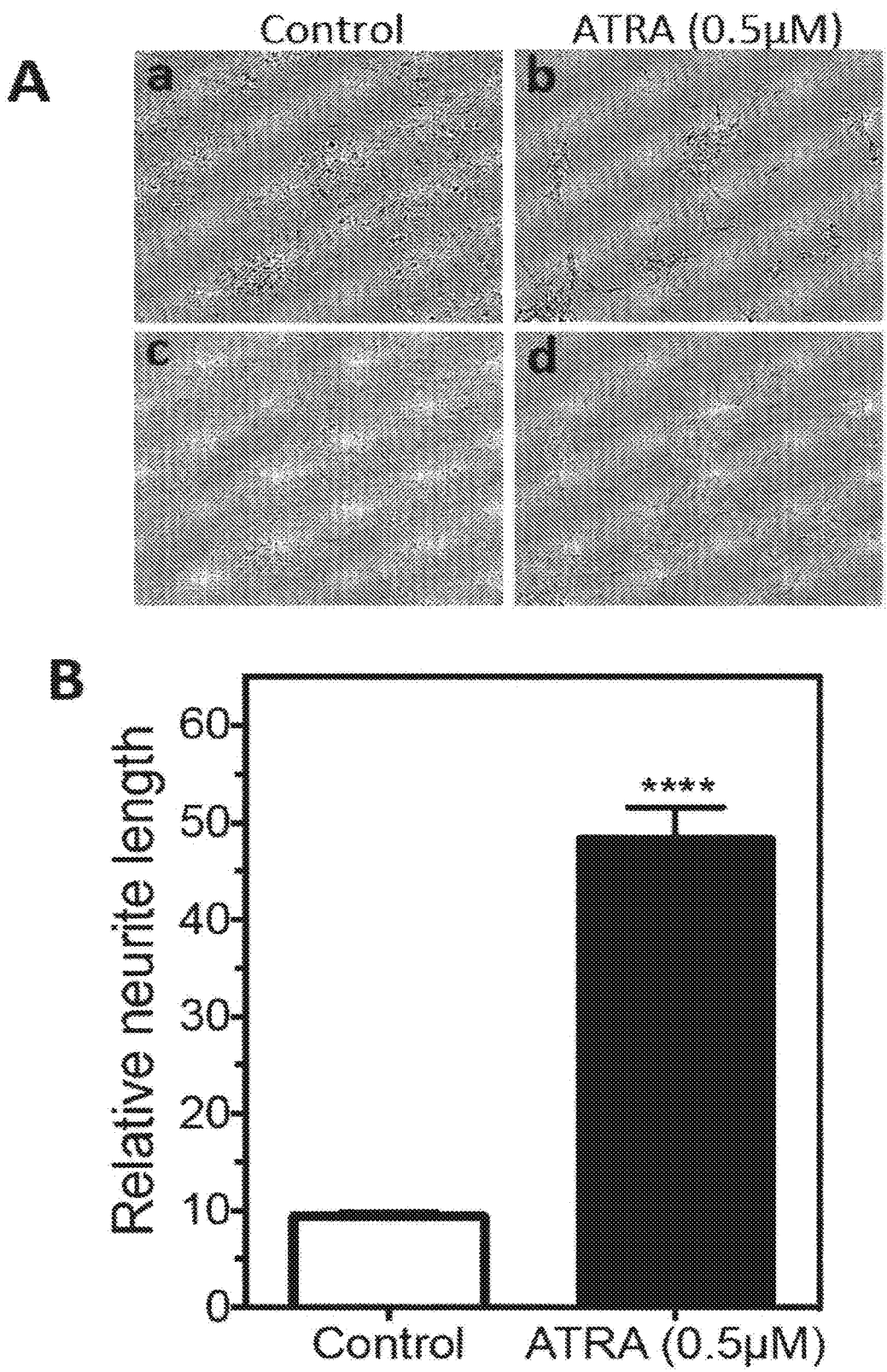
FIG. 1A-1F. Neurite length is a quantifiable differentiation marker of BE(2)-C cells. 2,500 cells were plated in 96-well plates and cultured overnight. Cells were then treated with ATRA or carrier (DMSO, control) and placed into the IncuCyte for detecting neurite outgrowth. Nine images were taken from each well to allow for statistical analysis. Relative neurite length is defined as neurite length per cell body area. (A) ATRA induces neurite outgrowth. Shown are representative phase-contrast images for cells treated with (a) carrier or (b) ATRA for 5 days, and (c, d) the same images analyzed to define neurites and cell body areas. (B) Quantification shows that ATRA significantly increases the relative neurite length compared to control. (C) Relative neurite lengths increase in a time-dependent manner during ATRA-induced cell differentiation. Neurite lengths were normalized to the starting time point (0 h). (D) Dose-dependent effect of ATRA on neurite outgrowth. Shown are the results after treating with ATRA for 5 days. (E) Dose-dependent effect of ATRA on cell viability. Cells were treated with different concentrations of ATRA, and cell viability was determined after 5 days. (F) Dose dependent effect of ATRA on the expression levels of cell differentiation markers GAP43, NSE and β tubulin III, cell proliferation markers Ki67 and PCNA, and apoptotic markers cleaved CASPASE 3 and PARP. Cells were treated with ATRA as above, and protein levels were determined by Western blots after 5 days. , $p<0.01$; *, $p<0.001$; ****, $p<0.0001$.

A HCS approach was developed to facilitate the discovery of novel differentiation-inducing agents for neuroblastoma. Several HCS approaches based on quantification of neurite outgrowth have been described (Radio et al., *Toxicol Sci*, 2008, 105(1):106-18); Yeyeodu et al., *Curr Chem Genomics*, 2010, 4:74-83; Price et al., *J Biomol Screen*, 2006, 11(2): 155-64; Mitchell et al., *J Neurosci Methods*, 2007, 164(2):

350-62). However, quantifications of neurite outgrowth in these approaches were either based on cell lines engineered to express fluorescent reporters or involve staining of fixed cells (Radio et al., *Toxicol Sci,* 2008, 105(1):106-18; Yeyeodu et al., *Curr Chem Genomics,* 2010, 4:74-83; Price et al., *J Biomol Screen,* 2006, 11(2):155-64; Mitchell et al., *J Neurosci Methods,* 2007, 164(2):350-62). These approaches are generally time-consuming. In addition, whether the extent of neurite outgrowth in neuroblastoma cells is a reliable marker to evaluate the potency of differentiation-inducing agents was not clearly characterized. Here it is shown that, in neuroblastoma cell line BE(2)-C, neurite length of differentiated cells is quantifiable based on phase-contrast images of live cells and is a reliable marker of the extent of cell differentiation. This HCS approach was used to examine neuroblastoma cell differentiation by quantifying neurite outgrowth. The neurite length distribution of untreated cells fits Gamma model, so in certain aspects this model was used to perform statistical analysis on neurite-based HCS. Screening of a library of miRNA mimics demonstrates that the screening and statistical analysis methods are specific and sensitive for identifying differentiation-inducing agents. This approach will facilitate future discovery of differentiation-inducing drugs and drug targets for treating neuroblastoma.

The studies described herein provide comprehensive and direct functional analysis of miRNA species in inducing neuroblastoma cell differentiation. The screen not only recapitulated several previous findings, but also identified miRNAs that have not been known to regulate neuroblastoma differentiation. For example, methods identified the function of miR-506-3p (mature sequence=uaaggcacccuucugaguaga (SEQ ID NO:1) in promoting neuroblastoma cell differentiation. Further investigations show that endogenous miR-506-3p expression was dramatically increased in differentiated neuroblastoma cells. In addition, published data have indicated the tissue-specific expression of miR-506 in adrenal gland, the primary tissue of origin for neuroblastoma (Liang et al., *BMC Genomics,* 2007, 8:166). This evidence altogether implicated the important role of miR-506-3p in neuroblastoma pathogenesis. Comprehensive analysis of miRNAs in neuroblastoma cell differentiation is a step towards elucidating the entire picture of miRNA involvement in differentiation.

In the HCS studies described herein, several miRNAs that were previously reported to induce neuroblastoma cell differentiation were not identified as potent inducers of cell differentiation (Le et al., *Mol Cell Biol,* 2009, 29(19):5290-305; Foley et al., *Cell Death Differ,* 2011, 18(7):1089-98). One possible explanation of this result is that the miRNAs function in a cell specific context, and the screen described herein was conducted in a different cell line from those used in previous studies.

Another finding of the studies described herein is the overrepresentation of a set of miRNA seed families in the identified differentiation-inducing miRNAs. This observation leads to a conclusion that the conservation of seed sequence among different miRNAs located at different genomic regions may be an important evolution trait that is selected by nature to guard the normal cell differentiation process during development; if one miRNA fails in its expression in cells, expression of another seed-family member will perform similar function to prevent differentiation error. If this is true, it is expected that miRNA seed sequence families are more likely to be involved in cell differentiation than miRNAs with unique sequences.

Previous studies have demonstrated the promise of synthetic miRNA mimics as therapeutic agents in cancer treatment (Kota et al., *Cell,* 2009, 137(6):1005-17; Trang et al., *Mol Ther,* 2011, 19(6):1116-22). Identification of novel differentiation-inducing miRNA mimics provides a group of novel candidates to treat neuroblastoma. The identification of several seed-sequence families that are potent differentiation inducers reinforces the notion that miRNA seed sequences play the key role in defining their biological function, which provides the rationale for developing synthetic seed sequence-based oligos as differentiation-inducing agents. By replacing the nucleic acids in the non-seed positions while keeping the seed sequence unchanged, various seed sequence-based synthetic oligos can be designed in order to identify the optimal design that has the most potent effect on neuroblastoma differentiation and has minimal non-specific cytotoxicity on normal cells and tissues. In certain aspects a miRNA mimic comprises a seed sequence of aaggcac (SEQ ID NO:3).

Currently, differentiation agents are limited to be used for post-remission maintenance therapy in high-risk neuroblastoma (Park et al. *Hematol Oncol Clin North Am,* 2010, 24(1):65-86). One of the reasons for this limitation is that the currently available differentiation agents are not as potent as other anti-cancer agents in ablating cancer cells. However, the studies described herein show that a miR-506-3p mimic reduced neuroblastoma cell viability to a much greater extent than cis-RA.

In certain aspects targetomes are predicted based on the top 14 differentiation-inducing miRNAs identified using informatics tools. The studies suggest that the differentiation-inducing function of a miRNA is likely mediated by concordantly down-regulating multiple targets. It is highly likely that there are undiscovered targets of these miRNAs that play important roles in mediating their differentiation-inducing functions. Indeed, expression array analyses indicate that miR-506-3p/miR-124-3p overexpression down-regulates many more targets than those investigated in the studies described herein.

A HCS platform has been established to screen for novel differentiation-inducing substances in neuroblastoma cells. New miRNAs and miRNA seed families that induce neuroblastoma cell differentiation have been identified. The study not only provides an understanding of the role of miRNAs in neuroblastoma differentiation, but also provides novel leads for developing miRNA-based differentiation agents for neuroblastoma treatment.

Figure 1C:
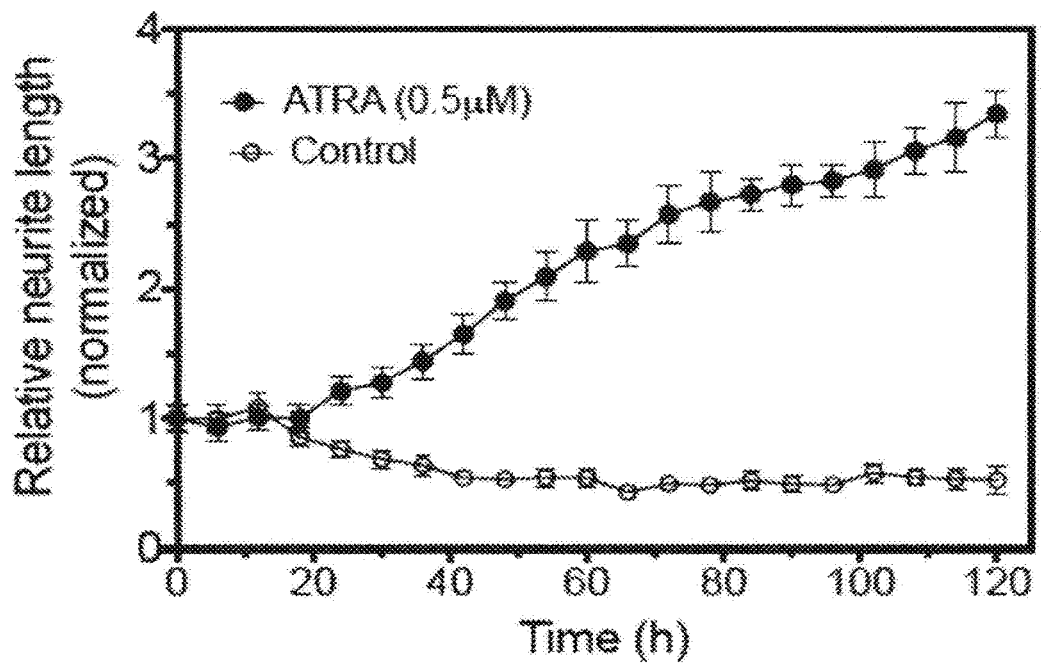
Figure 1D:
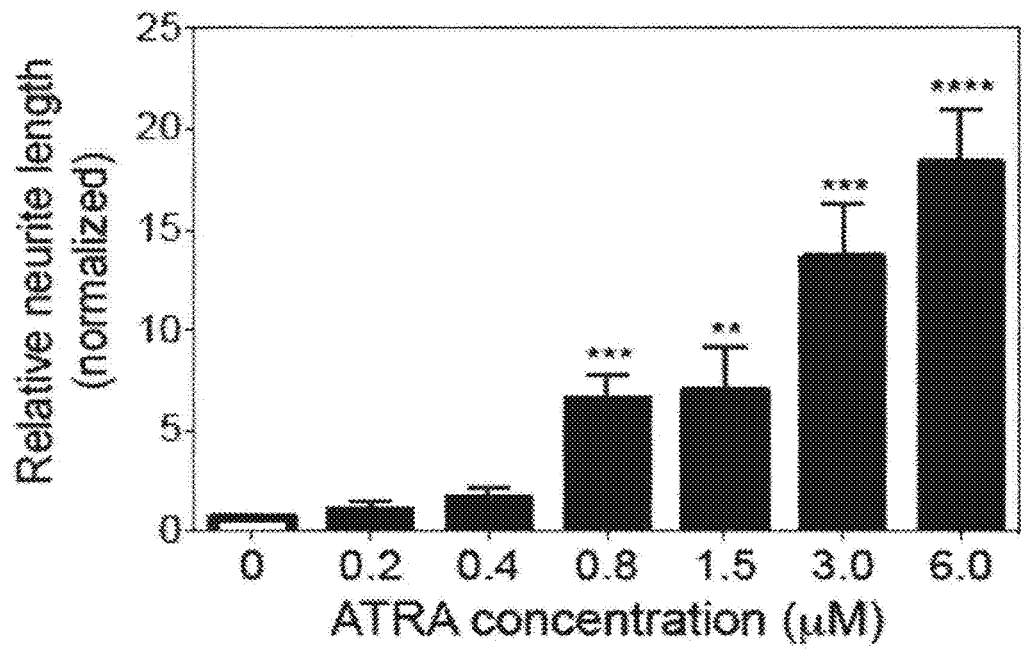
Figures 1E, 1F:
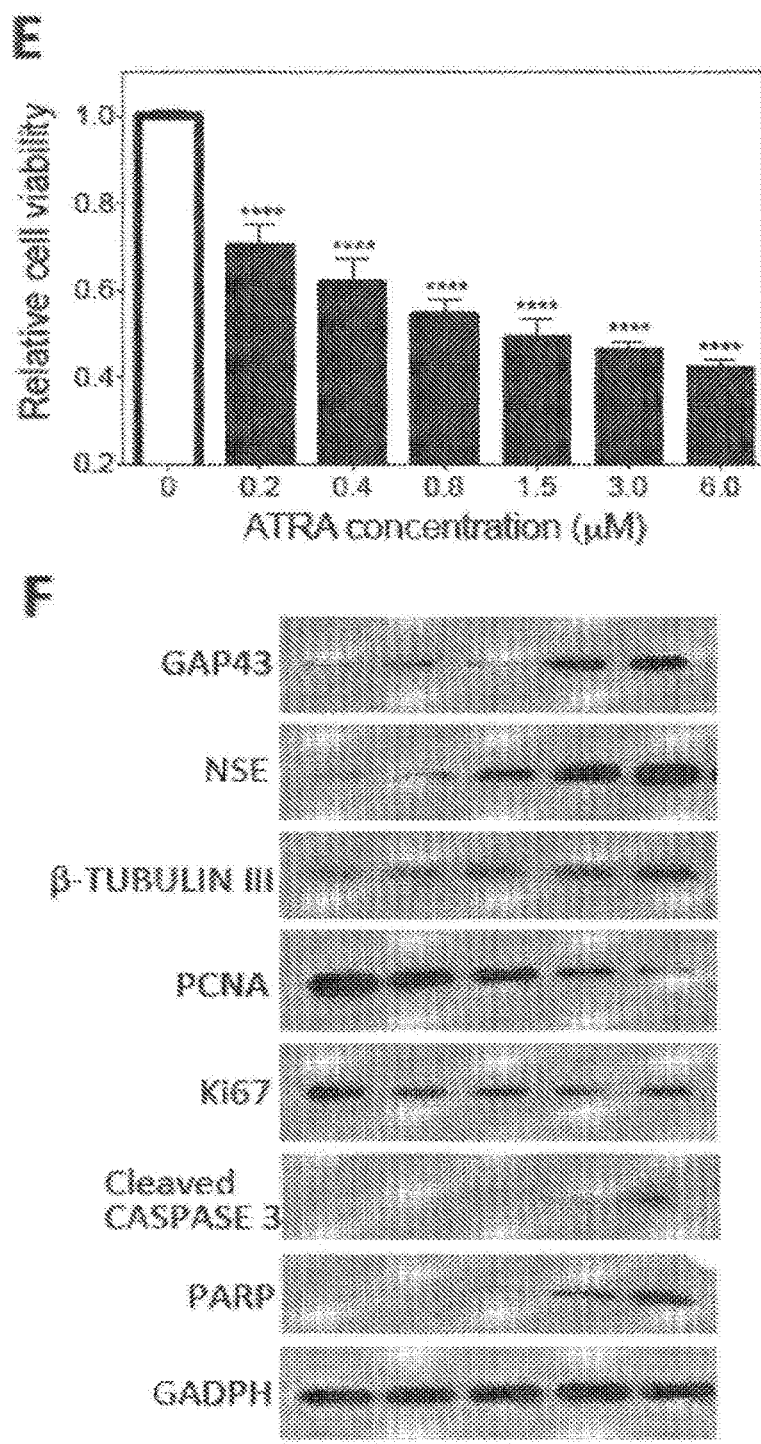

A HCS Approach for Measuring Neuroblastoma Cell Differentiation is Developed Based on Neurite Quantification. Neurite outgrowth is well recognized as a morphological hallmark of neuroblastoma cell differentiation in vitro (Thiele et al., *Nature,* 1985, 313(6001):404-06; Pahlman et al., *Int J Cancer,* 1981, 28(5):583-89; Reynolds and Perez-Polo, *J Neurosci Res,* 1981, 6(3):319-25; Prasad and Kumar, *Cancer,* 1975, 36(4):1338-43). This facilitates the development of a HCS approach to identify differentiation-inducing agents based on quantification of neurite outgrowth. Neuroblastoma cell line BE(2)-C shows easily detectable neurite outgrowth upon induced differentiation by all-trans retinoic acid (ATRA). As shown in FIG. 1A, ATRA (b) induces dramatic neurite outgrowth in BE(2)-C compared to control (a), and the neurites and cell body area can be clearly defined (c, d). Quantification (FIG. 1B) shows that ATRA significantly increases the relative neurite length compared to control. In addition, ATRA induces neurite elongation in both time- and dose-dependent manners (FIG. 1C-1D). Correspondingly, ATRA decreases cell viability (FIG. 1E), stimulates expression of neuroblastoma differentiation markers (i.e., growth associated protein 43 (GAP43), neuron specific enolase (NSE) and β-TUBULIN III)(Radio et al., *Toxicol Sci,* 2008, 105(1):106-18; Cheung et al., *Neurotoxicology,* 2009, 30(1):127-35; Mao et al., *Cancer Res,* 2011, 71(12):4314-24), inhibits expression of cell proliferation markers (i.e., PCNA and Ki67), and increases expression of apoptosis markers (i.e., cleaved CASPASE 3 and PARP) (FIG. 1F) in dose-dependent manners. These results indicate that neurite length is a reliable quantitative marker of BE(2)C cell differentiation, and therefore can be used to compare the efficacy of differentiation-inducing agents. This was the basis for the HCS protocol for identifying novel differentiation-inducing miRNAs.

Figures 2A, 2B:
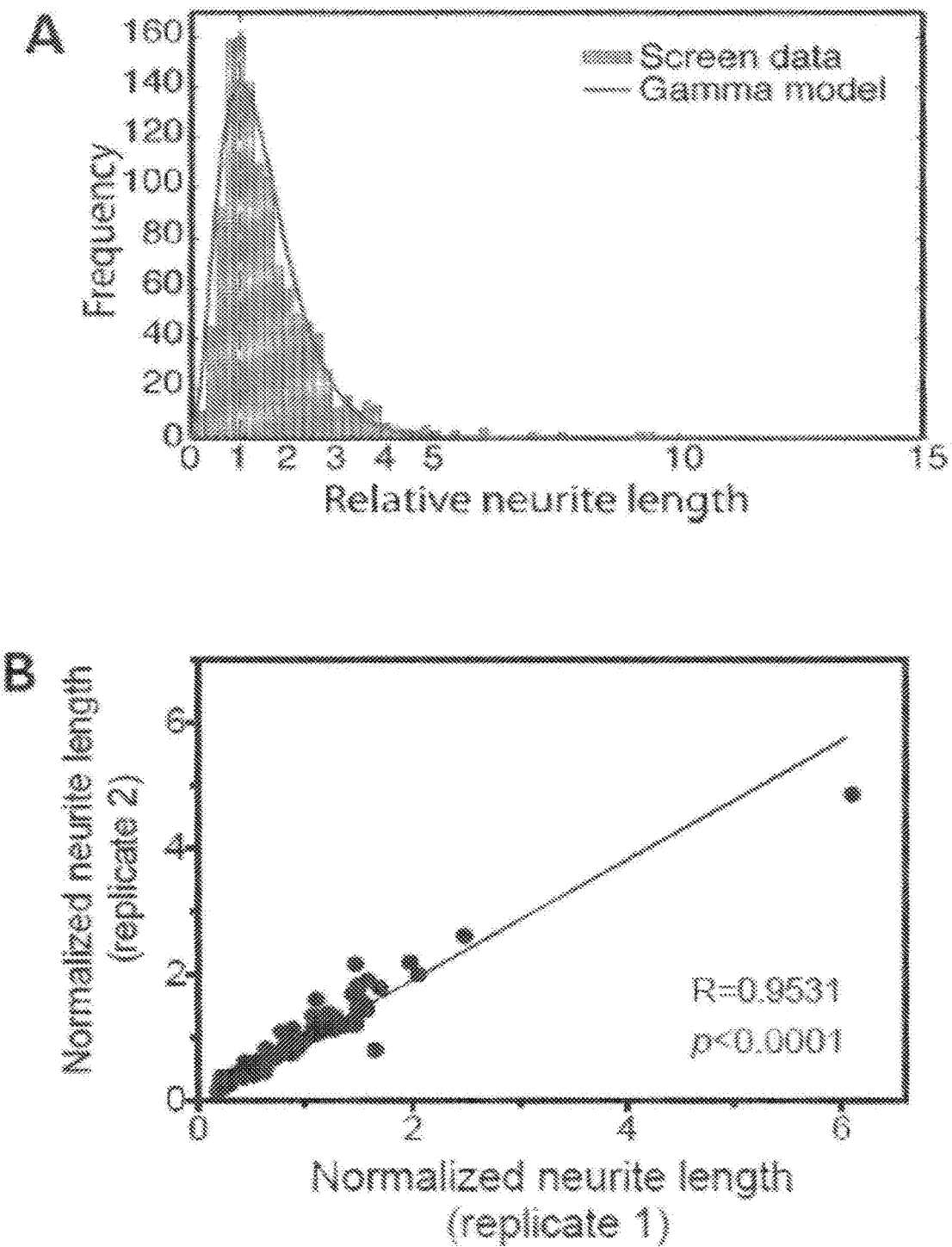
FIG. 2A-2C. HCS screening of miRNA mimics identifies miRNAs that induce neurite outgrowth in BE(2)-C cells. (A-B) 2,500 cells were reverse-transfected with 25 nM miRNA mimics in 96-well plates. After 4 days transfection, relative neurite lengths were quantified as above. (A) The distribution of post-normalized neurite length measurements (grey histogram) for individual miRNA mimics from the screen and the fitted Gamma distribution curve (⌴=3.27, ⌴=0.444) (B) Correlation between two independent neurite length measurements for one library plate. Cells were transfected with 25 nM mimics in two independent 96-well plates. Normalized neurite lengths were measured as above. Correlation of neurite length between the two plates was analyzed using two-tailed Pearson Correlation with $p<0.05$ considered significant. (C) The distribution of the neurite lengths for untreated BE(2)-C cells. 2,500 Cells were plated into each well in 96 well plates. After 4 days of culture, neurite lengths were analyzed as above. Shown are the neurite length distribution histogram, the empirical density curve, and the fitted Gamma distribution curve (⌴=30.23, ⌴=0.033). Using the $P<0.05$ threshold, Kolmogorov-Smirnov goodness-of-fit test for Gamma model validity did not reject the null hypothesis ($p=0.16$), which support that the neurite length distribution fit Gamma model.
Figure 2C:
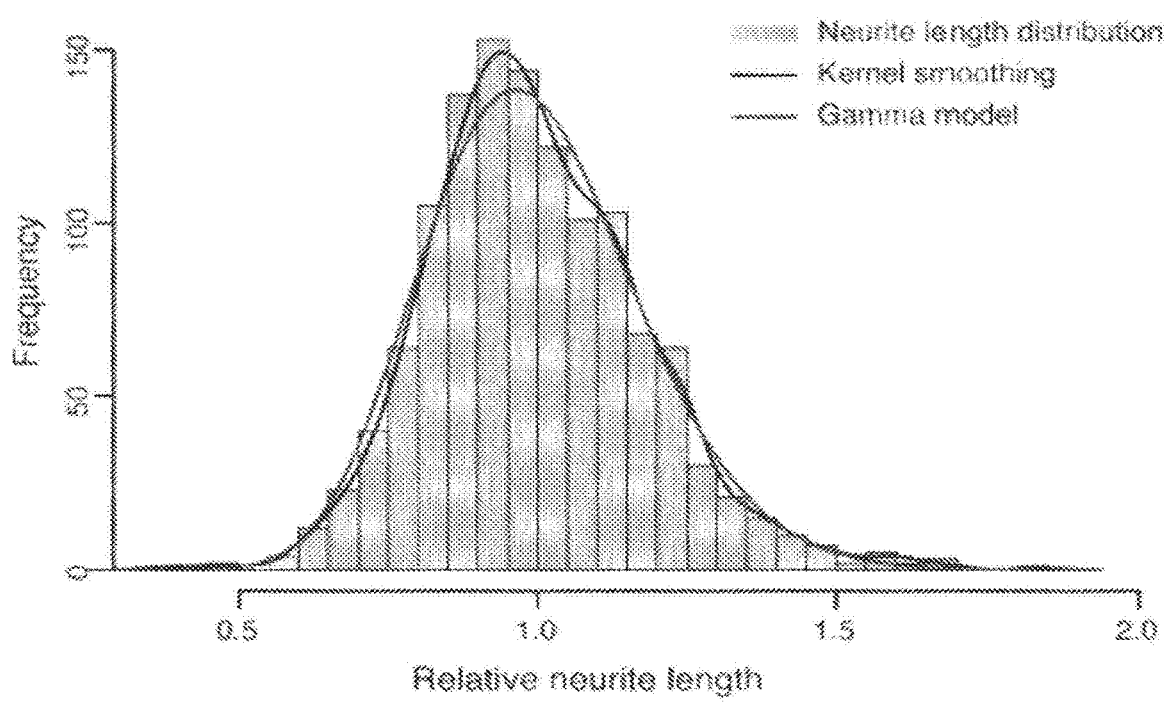

HCS Identifies Novel miRNAs that Induce Neuroblasoma Cell Differentiation. Using the HCS protocol, a library of miRNA mimics (Dharmacon) were screened in BE(2)-C cells. FIG. 2A shows the neurite length distribution associated with individual miRNA mimics. Replicate screens for one library plate from two independent transfections show that the results are highly reproducible (FIG. 2B) (R=0.95, $p<0.0001$), supporting the reliability of the screen. As shown in FIG. 2A, the neurite length distribution following treatment with miRNA mimics is asymmetric; a small fraction of miRNAs is identified as dramatically increasing neurite lengths on the far right side of the distribution. In order to examine the neurite length distribution of unaffected cells, 13 plates of untreated BE(2)-C cells were measured (FIG. 2C). Kolmogorov-Smirnov goodness-of-fit test for Gamma model validity indicates that the neurite length distribution fit Gamma model (p=0.16), which informs us to use this model (FIG. 2A) to assess the effect of individual miRNAs. Fourteen miRNA mimics were identified as significantly increasing neurite length using False Discovery (FDR) threshold <0.01 (Table 1). Using the same threshold, 0 hits were generated from untreated cells, indicating the specificity of the analysis approach. Among the 14 miRNAs, several were related to neuroblastoma cell differentiation in previous studies (Table 1)(Makeyev et al., *Mol Cell,* 2007, 27(3):435-48; Annibali et al., *PLoS One,* 2012, 7(7):e40269; Smith et al., *PLoS One,* 2010, 5(6):e11109; Silber et al., *BMC Med,* 2008, 6:14), demonstrating the sensitivity of the HCS approach.

TABLE 1

Fourteen miRNA mimics identified from HCS as inducing neurite outgrowth using a FDR threshold <0.01.

| (a) miRNA | (b) Neurite length (mean ± SD) | (c) p value | (d) FDR | (e) Mature sequence 5'-3' |
|---|---|---|---|---|
| hsa-miR-124-3p | 14.55 ± 4.75 | 1.11E-11 | 1.37E-08 | UAAGGCACGCGGUGAAUGCC (SEQ ID NO: 2) |
| hsa-miR-135b-5p | 14.02 ± 4.29 | 3.26E-11 | 2.02E-08 | UAUGGCUUUUCAUUCCUAUGUGA (SEQ ID NO: 6) |
| hsa-miR-506-3p | 10.04 ± 3.41 | 1.05E-07 | 4.34E-05 | UAAGGCACCCUUCUGAGUAGA(1) (SEQ ID NO: 1) |
| hsa-miR-34a-5p | 9.49 ± 3.18 | 3.11E-07 | 8.81E-05 | UGGCAGUGUCUUAGCUGGUUGU(2) (SEQ ID NO: 7) |
| hsa-miR-103a-3p | 9.43 ± 2.67 | 3.56E-07 | 8.81E-05 | AGCAGCAUUGUACAGGGCUAUGA(3) (SEQ ID NO: 8) |
| hsa-miR-450b-3p | 9.26 ± 2.64 | 4.94E-07 | 1.02E-04 | UUGGGAUCAUUUUGCAUCCAUA (SEQ ID NO: 9) |
| hsa-miR-449a | 9.16 ± 2.47 | 6.03E-07 | 1.07E-04 | UGGCAGUGUAUUGUUAGCUGGU(2) (SEQ ID NO: 10) |
| hsa-miR-2110 | 9.00 ± 2.40 | 8.21E-07 | 1.27E-04 | UUGGGGAAACGGCCGCUGAGUG (SEQ ID NO: 11) |
| hsa-miR-34b-5p | 8.41 ± 2.16 | 2.66E-06 | 3.66E-04 | UAGGCAGUGUCAUUAGCUGAUUG (SEQ ID NO: 12) |
| hsa-miR-107 | 7.60 ± 1.98 | 1.27E-05 | 1.55E-03 | AGCAGCAUUGUACAGGGCUAUCA(3) (SEQ ID NO: 13) |
| hsa-miR-3714 | 7.56 ± 1.91 | 1.37E-05 | 1.55E-03 | GAAGGCAGCAGUGCUCCCCUGU (SEQ ID NO: 14) |
| hsa-miR-449b-5p | 7.40 ± 1.85 | 1.89E-05 | 1.95E-03 | AGGCAGUGUAUUGUUAGCUGGC(2) (SEQ ID NO: 15) |
| hsa-miR-137 | 7.03 ± 1.36 | 3.83E-05 | 3.65E-03 | UUAUUGCUUAAGAAUACGCGUAG (SEQ ID NO: 16) |
| hsa-miR-3937 | 6.93 ± 1.05 | 4.61E-05 | 4.08E-03 | ACAGGCGGCUGUAGCAAUGGGGG (SEQ ID NO: 17) |

Figure 3A:
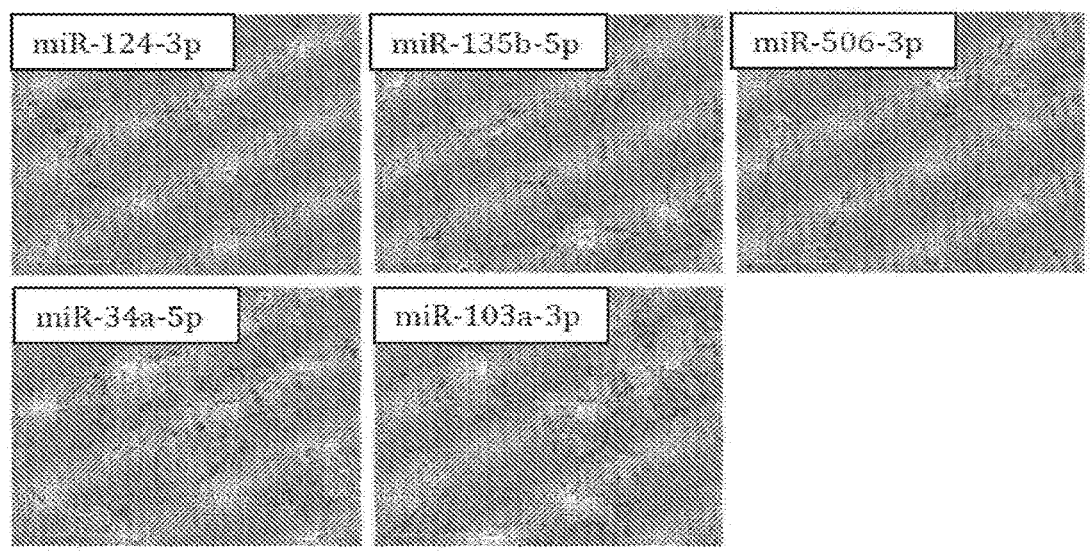
FIG. 3A-3G. Characterization of the effect of the top 5 neurite-inducing miRNA mimics on cell differentiation and growth in multiple neuroblastoma cell lines. (A-B) Effects of the identified top 5 miRNA mimics on neurite outgrowth. BE(2)-C cells were transfected with 25 nM miRNA mimics or control for 4 days, and relative neurite lengths were quantified as above. Shown are representative cell images analyzed to define neurite and cell body areas (A) and neurite length quantifications (B). (C) Effects of the 5 miRNA mimics on expression of differentiation markers. BE(2)-C cells were transfected with 25 nM of the indicated miRNA mimics or control, and proteins levels were examined after 4 days. (D) Effects of the 5 miRNA mimics on cell proliferation rate. (E) Effect of the 5 miRNAs on neurite outgrowth in multiple cell lines. Cells were transfected with 25 nM miRNA mimics or control, and neurite lengths were quantified as above after 5 days. (F-G) Effects of miR-506-3p (F) and miR-124-3p (G) mimics on expression of differentiation markers in multiple cell lines. *, $p<0.05$; , $p<0.01$; *, $p<0.001$; ****, $p<0.0001$.
Figure 3B:
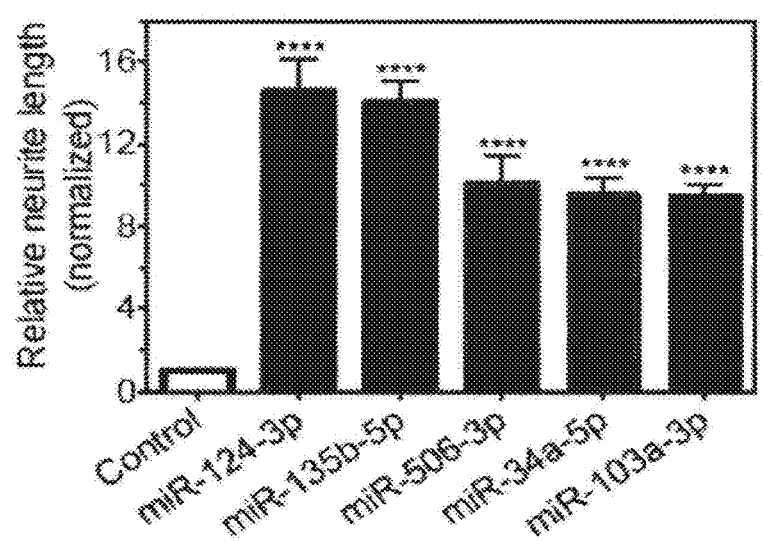
Figure 3C:
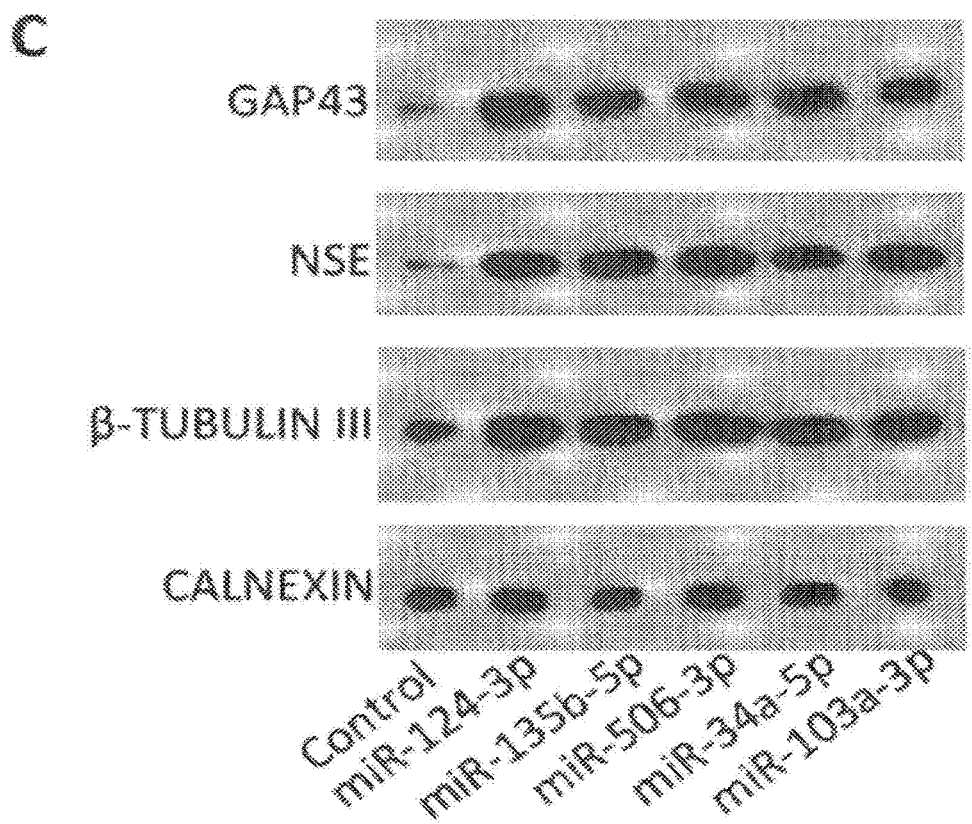
Figure 3D:
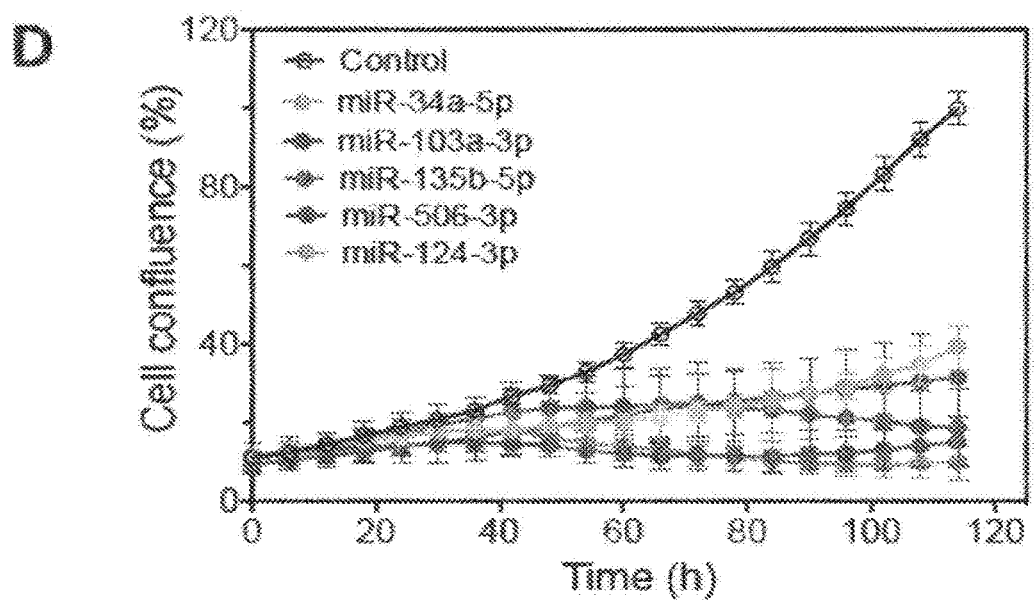
Figure 3E:
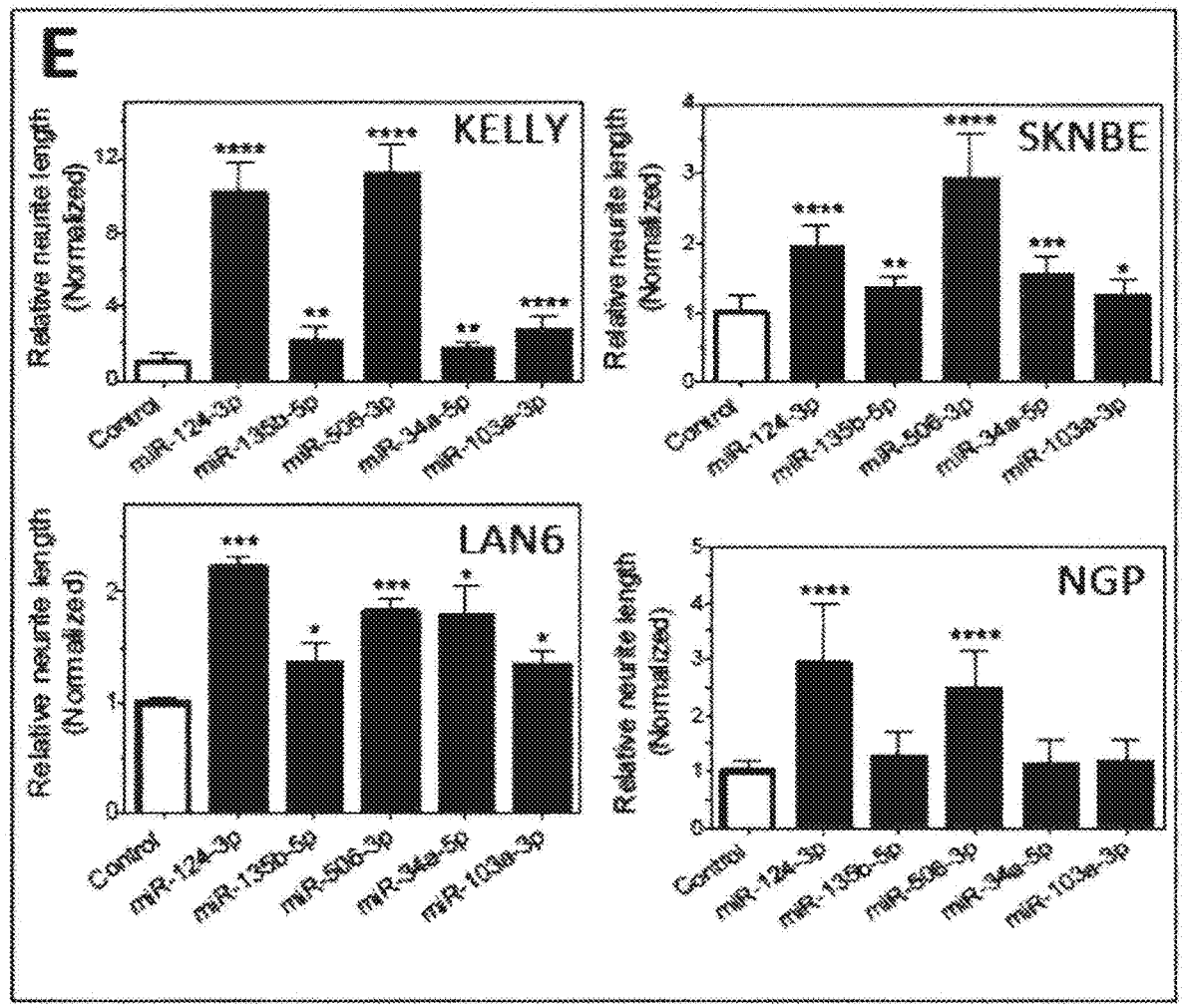
Figure 3F:
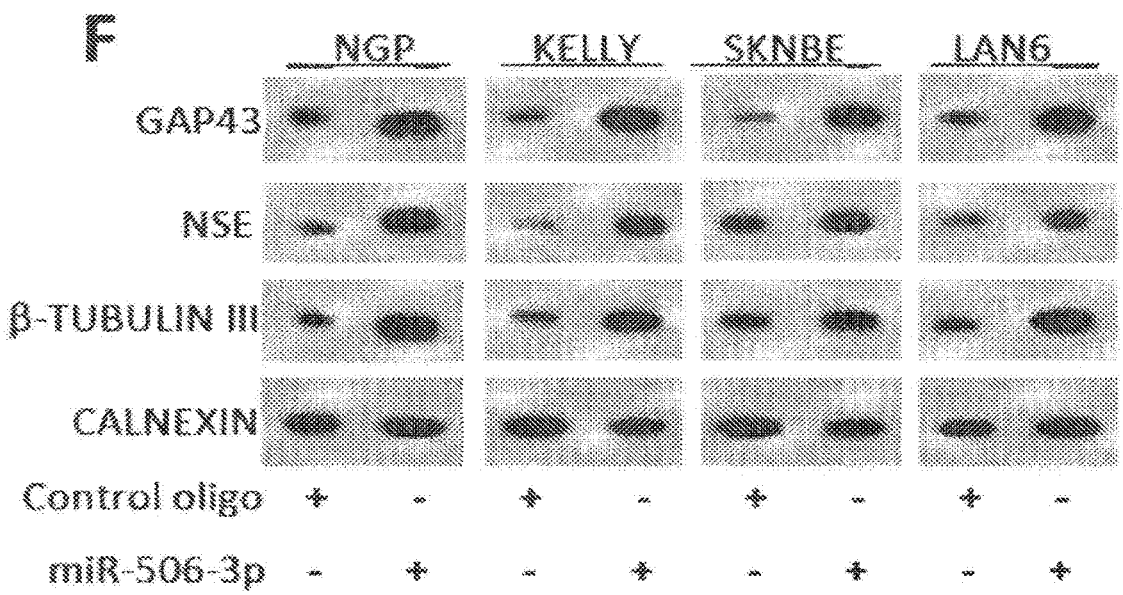
Figure 3G:
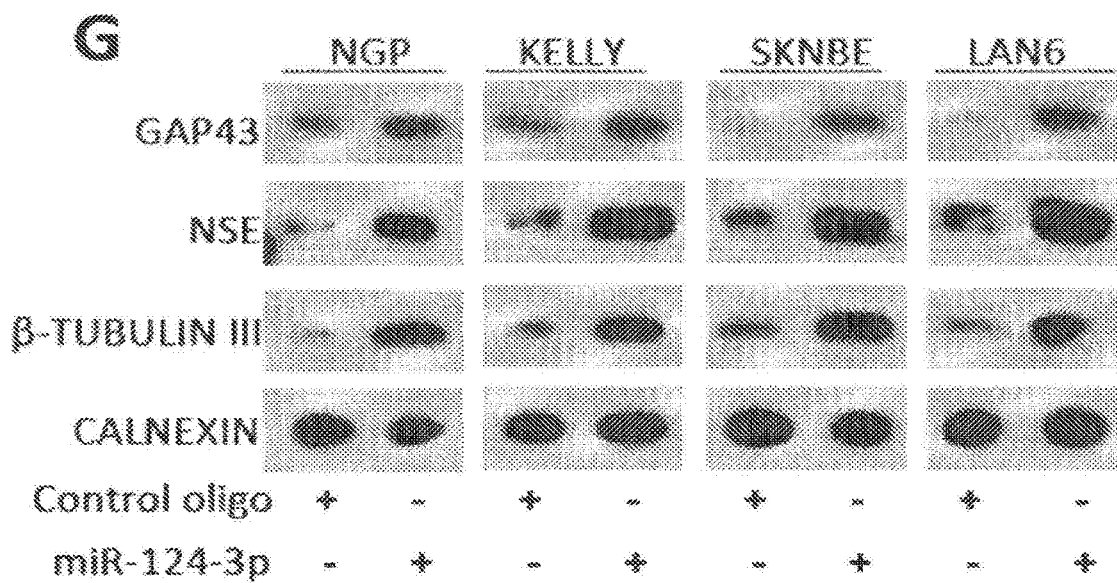
Figure 4A:
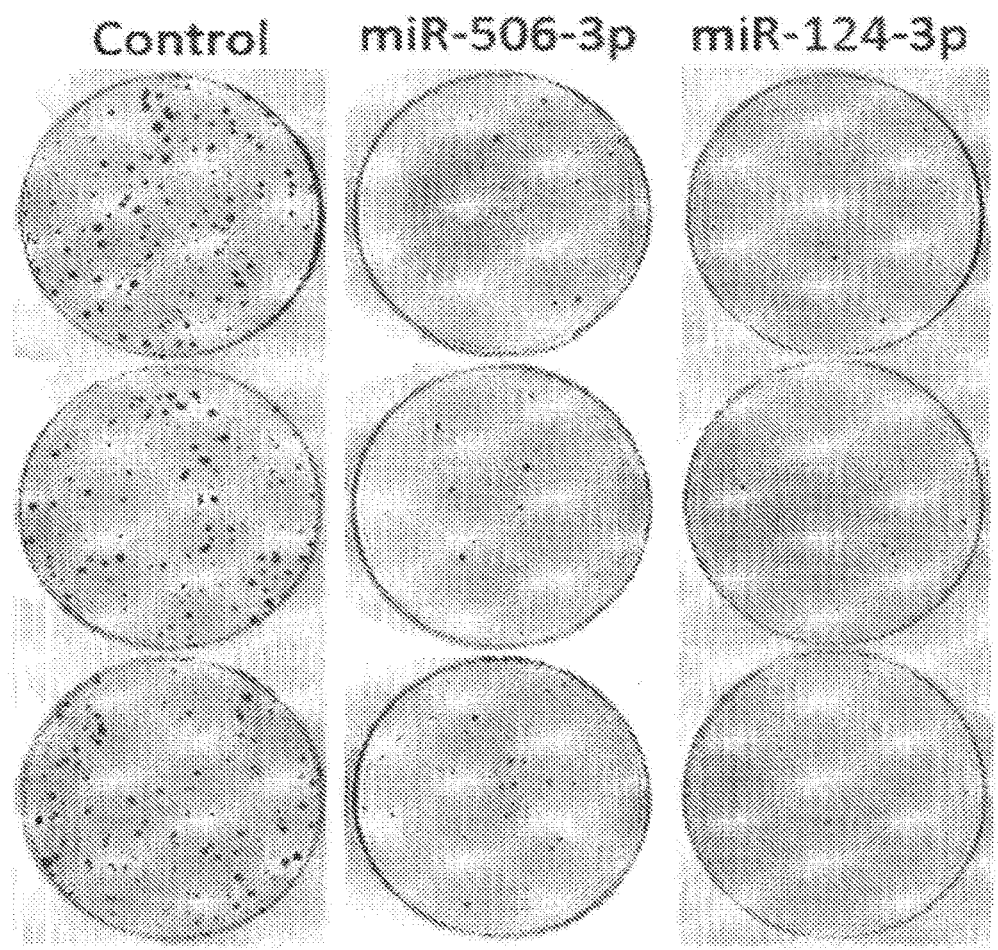
FIG. 4A-4H. Characterization of the tumor suppressive function of miR-506-3p/miR-124-3p family. (A-C) Colony formation assay as a function of miR-124-3p and miR-506-3p mimics. BE(2)-C cells were transfected with the 25 nM of the indicated oligos and colony formation were examined as above. Shown are (A) plate images of colony formation and quantified colony numbers (B) and sizes (C). (D-E) Effect of miR-124-3p and miR-506-3p precursors on neurite outgrowth. BE(2)-C cells were transfected with or without 10 nM miRNA precursors. Shown are (D) Representative images analyzed to define neurites and cell body areas after 4 days transfections and (E) quantification of relative neurite lengths. (F) Effect of cell differentiation on endogenous expression of miR-506-3p and miR-124-3p in BE(2)-C cells. (G) Dose-dependent effect of miR-506-3p mimic on neurite outgrowth in BE(2)-C cells. Cells were transfected with different concentrations of miR-506-3p mimic, and relative neurite lengths were quantified as above after 4 days. Neurite lengths were normalized to control (0 nM). (H) Dose-dependent effect of miR-506-3p mimic and cis-RA on cell viability in BE(2)-C cells. Cells were transfected with different concentrations of miR-506-mimic for 4 days or treated with different concentrations of cis-RA for 5 days, and cell viability was determined as above. *, $p<0.05$; , $p<0.01$; *, $p<0.001$; ****, $p<0.0001$.
Figure 4B:
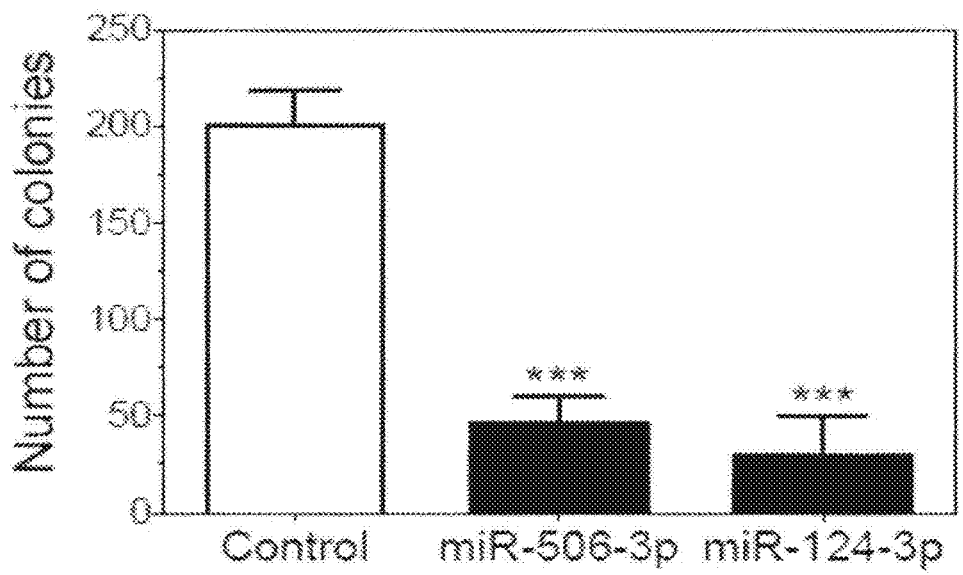
Figure 4C:
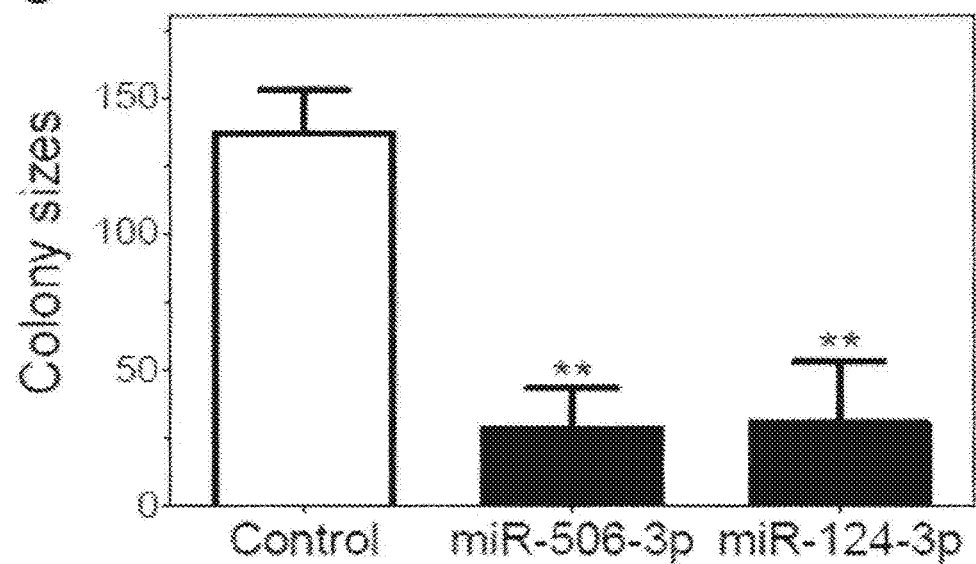
Figure 4D:
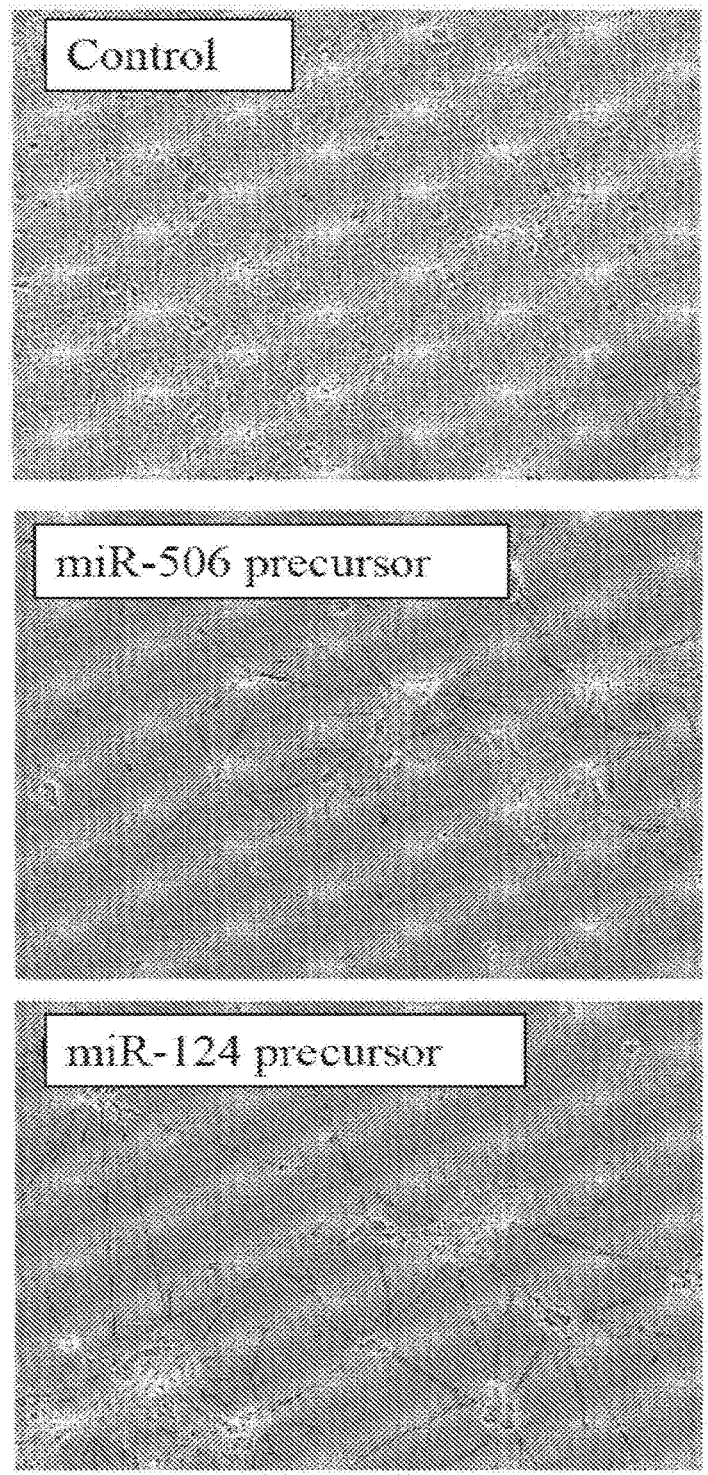
Figure 4E:
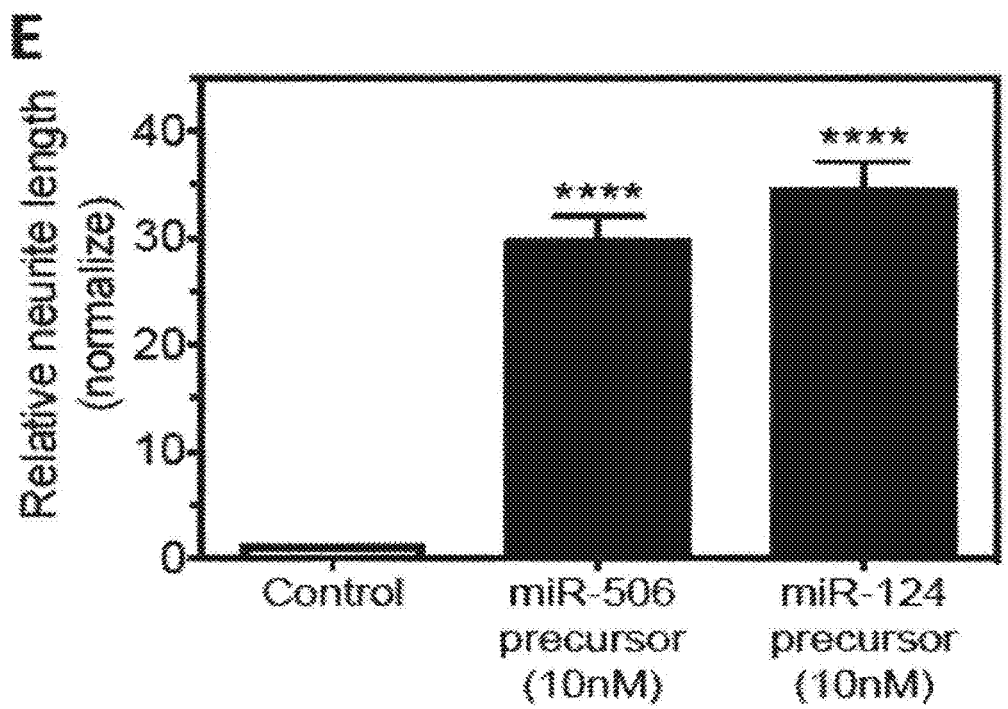

The differentiation-inducing functions of the top 5 microRNAs that are most potent in inducing neurite outgrowth were characterized (FIG. 3A-3B). Comparison to control, the 5 miRNAs induce expression of differentiation markers and dramatically decrease BE(2)-C cell growth rate (FIG. 3C-3D), demonstrating that true cell differentiation and growth arrest are induced. The 5 miRNAs were further tested in additional neuroblastoma cell lines with different genetic backgrounds. Among the 5 miRNAs, miR-506-3p and miR-124-3p, which belong to the same seed family (defined as a group of miRNAs that share common seed sequence, Table 1), have the most potent effect on neurite growth (FIG. 3E). Correspondingly, the two miRNAs dramatically induce expression of differentiation markers in all the tested cell lines (FIG. 3F-3G). It was shown that miR-506-3p and miR-I24-3p mimics significantly reduce the ability of BE(2)-C to form colonies, indicating their long-term capacity to inhibit cell proliferation (FIG. 4A-4C). To exclude the possibility that the induced cell differentiation and growth arrest are caused by off-target effects of the specific chemical designs of miRNA mimics, the effect of miR-506-3p and miR-124-3p precursors (Ambion) on differentiation were examined. The miRNA precursors are partially double-stranded RNAs designed to mimic the functions of the endogenous miRNAs, in contrast to the fully complementary double-stranded design of miRNA mimics. FIG. 4D-4E shows that the precursors significantly induced neurite outgrowth, recapitulating the results with miRNA mimics. This indicates that the differentiation-inducing function of miR-506-3p and miR-124-3p mimics is unlikely caused by off-target effect. Overall, the above results demonstrate the general and potent effect of miR-506-3p/miR-124-3p on inducing differentiation, suggesting the potential of restoring miR-506-3p and miR-124-3p expressions as a novel differentiation therapeutic strategy to treat neuroblastoma.

Figure 4F:
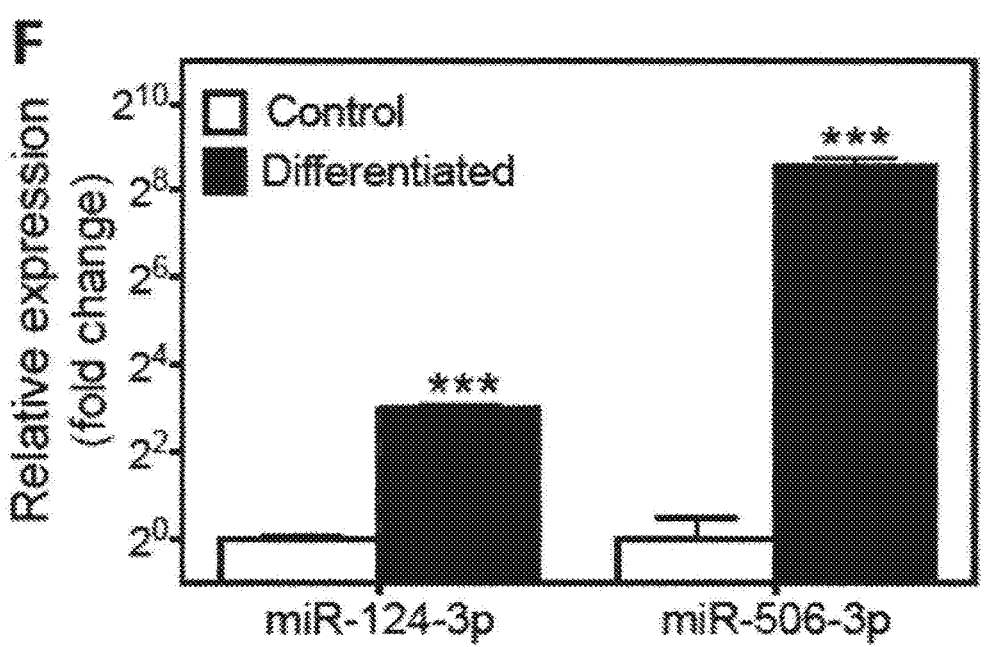
Figure 4G:
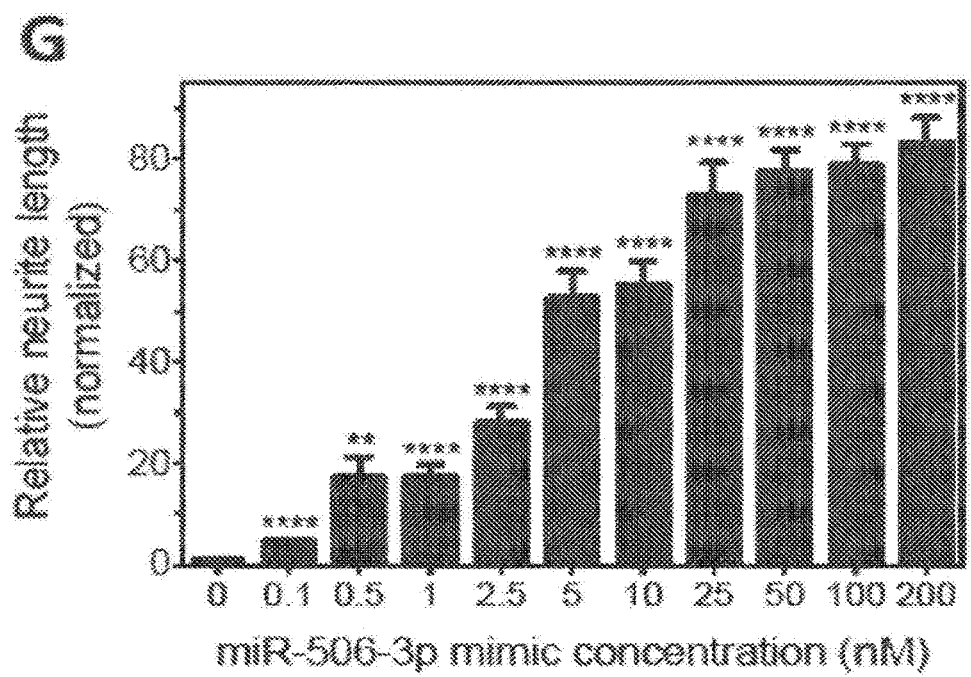
Figure 4H:
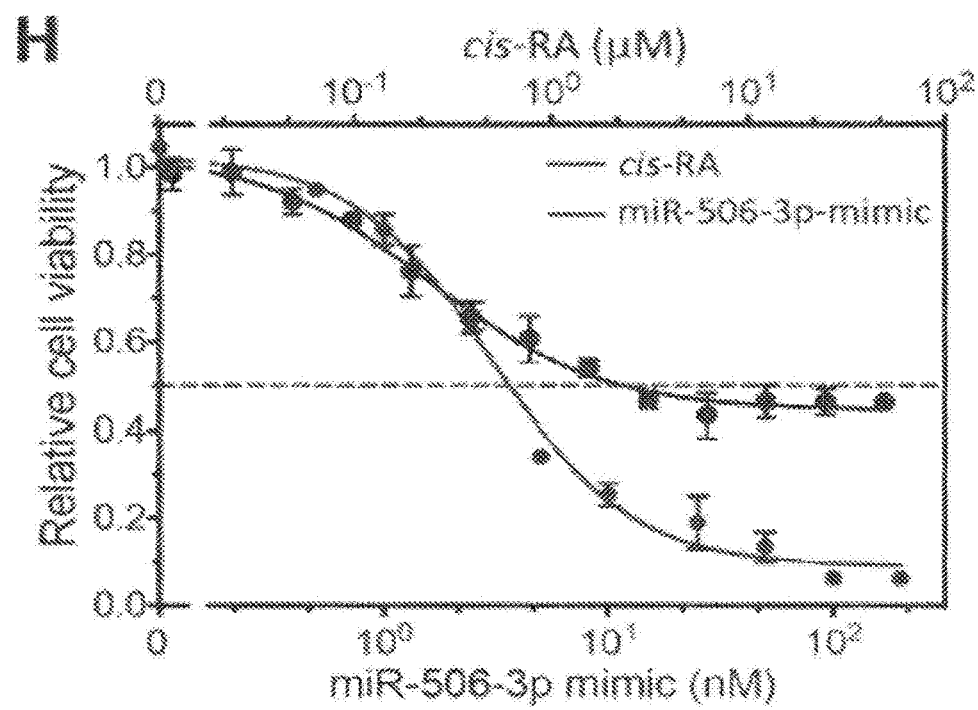

To further examine the potential pathophysiological relevance of endogenous miR-506-3p and miR-124-3p in regulating neuroblastoma differentiation, expression levels were measured in differentiated BE(2)-C cells. FIG. 4F shows that expressions of both miRNAs are significantly increased in differentiated cells. However, the overexpression of miR-506-3p (380.1±48.4 fold) is much more dramatic than that of miR-124-3p (8.1±0.4 fold). These results indicate that endogenous miR-506-3p expression in neuroblastoma cells is highly regulated and suggest that, relative to miR-124-3p, endogenous miR-506-3p is likely to be a more dominant driving force in controlling cell differentiation. It was observed that miR-506-3p mimic induces neurite outgrowth and decreases cell viability in a dose-dependent manner, and that the induction of neurite outgrowth is significant at a concentration as low as 0.1 nM (FIG. 4G-4H). FIG. 4H also shows that the cytotoxic effect of miR-506-3p mimic is much more potent (reducing cell viability to 6.3±0.3% when reaching plateau) than 13-cis retinoic acid (cis-RA) (42.6±3.7%), a differentiation-agent currently used to treat neuroblastoma patients (Matthay et al., J Clin Oncol, 2009, 27(7):1007-13). Altogether, these results demonstrate the potent function of miR-506-3p in inducing differentiation and in reducing cell survival and growth. The role of miR-506-3p in neuroblastoma tumorigenesis has not been investigated previously.

Figure 5:
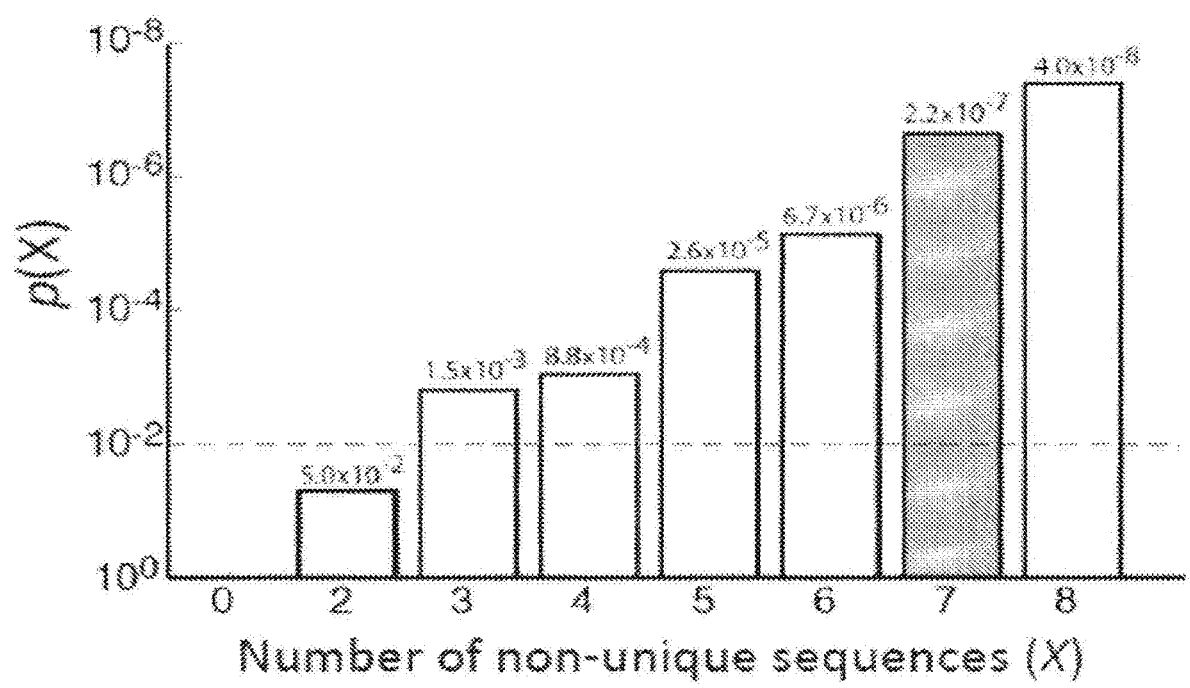
FIG. 5. Enrichment analysis of seed families in a set of 14 miRNAs by random permutation. Bar shows the probability ($p=2.2\times10^{-7}$) that at least 7 non-unique seed sequences appear in a randomly selected set of 14 miRNAs.

From the screen, miRNAs were also identified that significantly reduce cell survival but do not induce differentiation. This indicates that miRNAs modulate neuroblastoma cell survival and growth through distinct mechanisms, and cell differentiation is not a prerequisite for cell death or growth arrest, which supports the functional specificity of the identified differentiation-inducing miRNAs in regulating differentiation.

miRNA Seed Families that are Potent Inducers of Cell Differentiation are Discovered from HCS. miRNA seed sequences are central in determining their target genes (Krek et al., Nat Genet, 2005, 37(5):495-500; Lewis et al., Cell, 2005, 120(1):15-20; Stark et al., Cell, 2005, 123(6):1133-46; Laurent et al., Stem Cells, 2008, 26(6):1506-16). The seed sequences of the identified differentiation-inducing miRNAs were analyzed. Surprisingly, as shown in Table 1, three miRNA seed families, which accounts for 7 miRNAs, are identified within the 14 miRNAs. Enrichment analysis by random permutation shows that the probability that ≥7 non-unique seed sequences appear in a set of 14 randomly drawn miRNAs from the miRNA mimic library is $p=2.2 \times 10^{-7}$ (FIG. 5), indicating that miRNA seed-sequence families are significantly overrepresented in the identified 14 miRNAs. Further investigation of the remaining 7 miRNAs shows that the seed sequences of miR-135b-5p (shares seed sequence with miR-135a-5p), miR-34b-5p (shares with miR-449c-5p and miR-2682-5p) and miR-450b-3p (shares with miR-769-3p) are not unique. In addition, seed sequence family 2 includes another miRNA, miR-34c-5p, which is not identified in the top 14 candidates. Close examination of the screen results indicates that miR-34c-5p, miR-135a-5p and miR-449c-5p also increase the neurite lengths, ranking as 17th, 43th and 128th in the screen (miR-2682-5p was not in the library), although the effect of miR-449c-5p did not reach statistical significance using p<0.05 threshold. miR-769-3p does not induce neurite outgrowth, and, however, is the only exception among the identified differentiation-inducing seed families.

Figure 6:
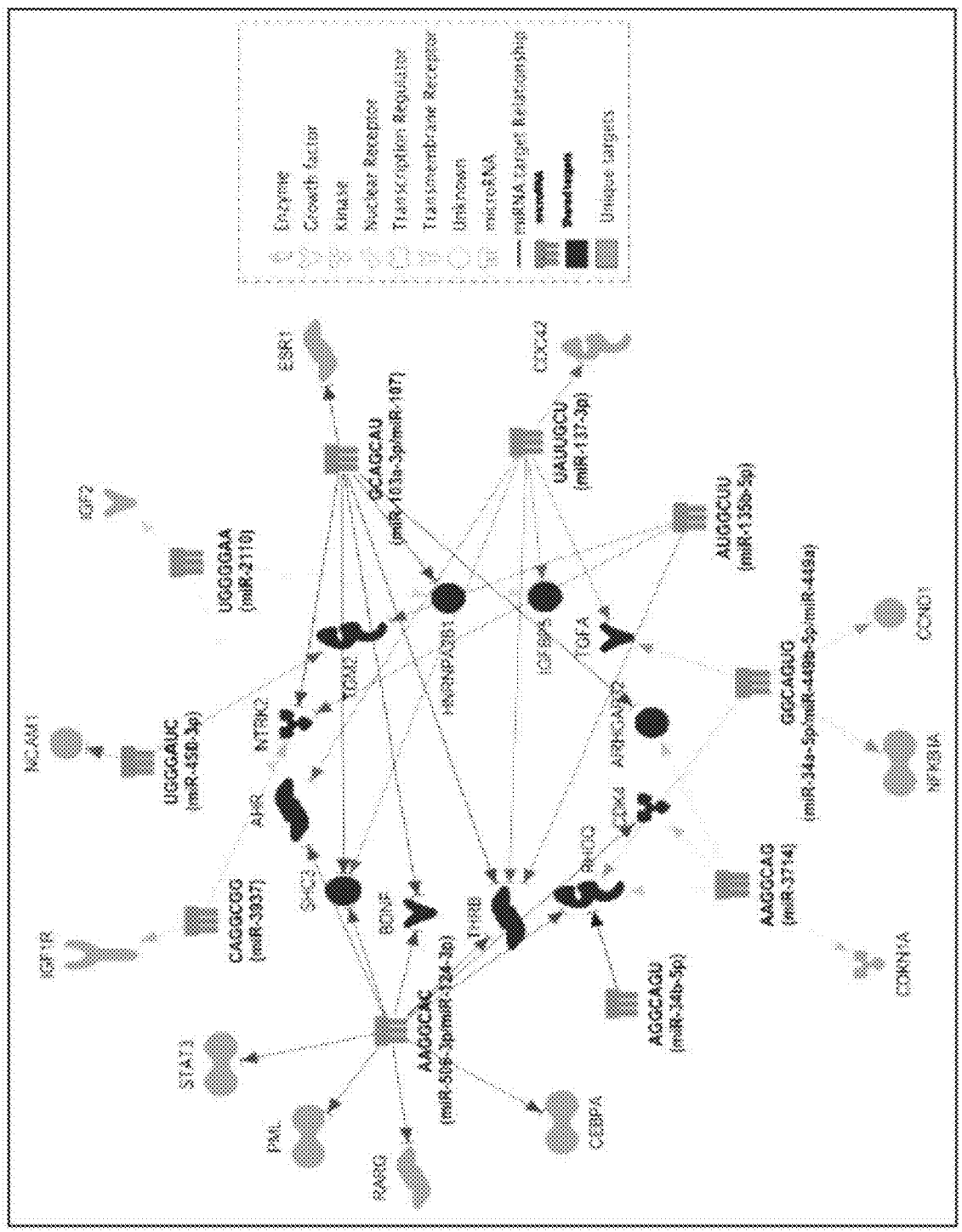
FIG. 6. The predicted differentiation-inducing targetome network for the identified 14 differentiation-inducing miRNAs. The 14 miRNAs were grouped into 10 seed-sequence groups. Predicted targets previously reported as involved in neuroblastoma differentiation were used to create the targetome network.

The Identified Differentiation-inducing miRNAs are Predicted to Target Distinct Spectra of Genes Involved in Neuroblastoma Differentiation. The above observations lead to the identification of potential miRNA targets based on seed sequence matches. 48 genes were identified that have been previously demonstrated to regulate neuroblastoma differentiation using Ingenuity Pathway Analysis (IPA) (Ingenuity System). Not surprisingly, further IPA miRNA target analysis indicates that each of the miRNAs/seed families is predicted to target multiple genes involved in neuroblastoma differentiation (FIG. 6), among which the miR-506-3p/miR-124-3p family is predicted to target 10 of the 48 genes. The results also show that, although the predicted targets of these miRNAs/seed-sequence families overlap, each miRNA/seed sequence family has a unique targetome, suggesting that they are likely to induce cell differentiation through distinct but overlapping pathways.

Figures 7A, 7B:
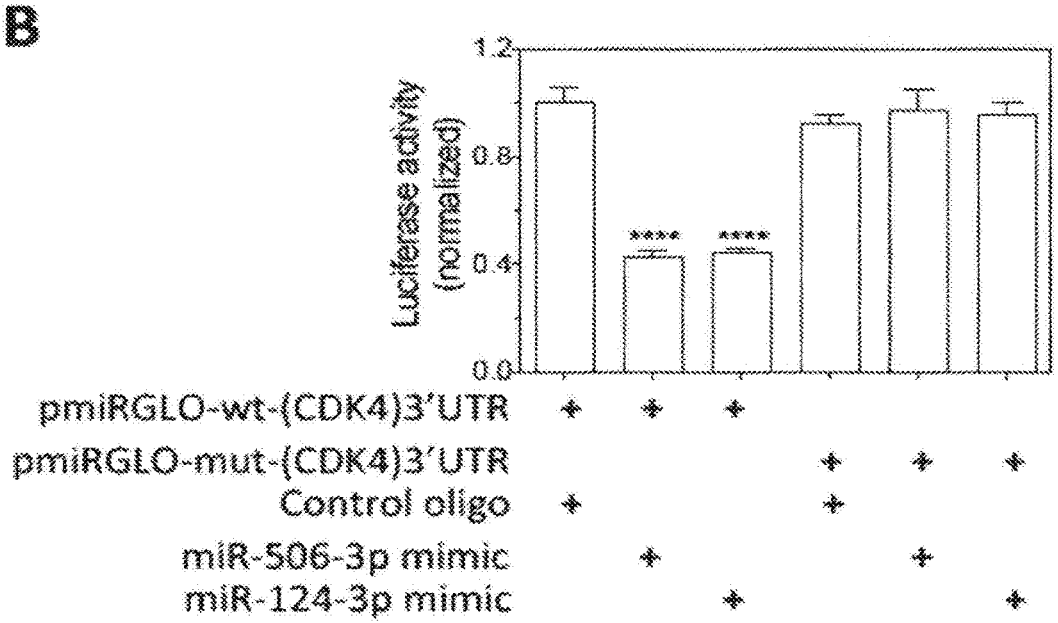
FIG. 7A-7F. Validation of CDK4 and STAT3 as direct targets that mediate the differentiation-inducing function of miR-506-3p and miR-124-3p. (A) The predicted interactions between miR-506-3p/miR-124-3p and the target sites in the 3'UTR of STAT3 and CDK4 mRNAs. The seed sequences are underlined. (SEQ ID NOS: 1, 2, 18, 19, 20, 21) (B-C) Validation of the target sites of miR-506-3p and miR-124-3p in the 3'UTRs of (B) CDK4 and (C) STAT3 by luciferase reporter assay. BE(2)-C cells were co-transfected with the indicated vectors and miRNA mimics or control oligo. After 72 h of transfection, cells were lysed and luciferase activity was measured. Shown are normalized luciferase activities of different treatment groups. (D) miR-506-3p and miR-124-3p overexpression down-regulate endogenous CDK4 and STAT3 protein expression levels. Cells were transfected as above for 4 days, and protein levels were measured by Western blots. (E-F) Effect of CDK4 and STAT3 knockdown on neurite outgrowth in BE(2)-C cells. Cells were transfected with the indicated oligos, and neurite lengths were measured as above after 4 days transfection. Shown are representative cell images analyzed to define neurites and cell body areas (G) and quantification of neurite length under the indicated treatment conditions (H). , $p<0.01$; *, $p<0.001$; ****, $p<0.0001$.
Figures 7C, 7D:
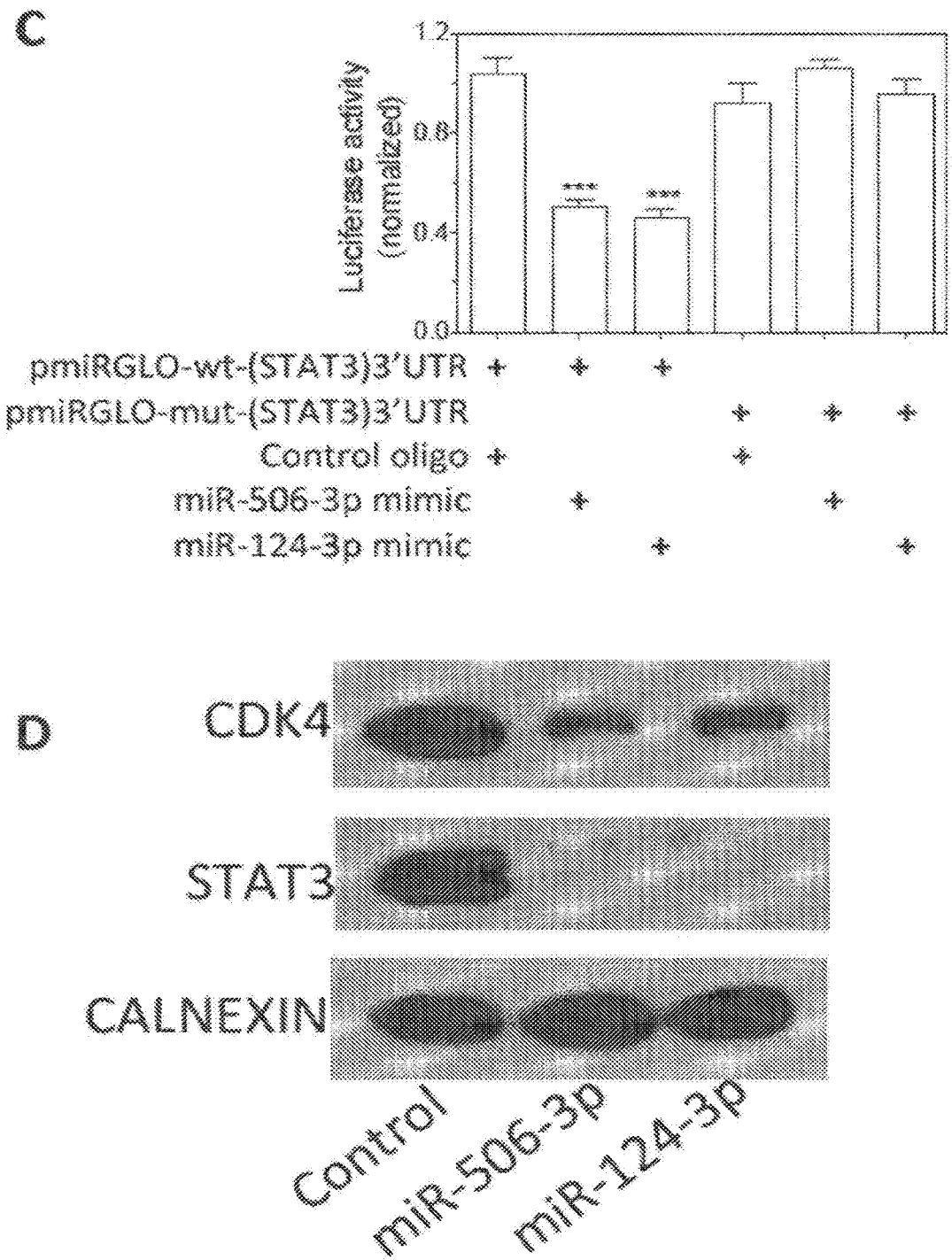
Figures 7E, 7F:
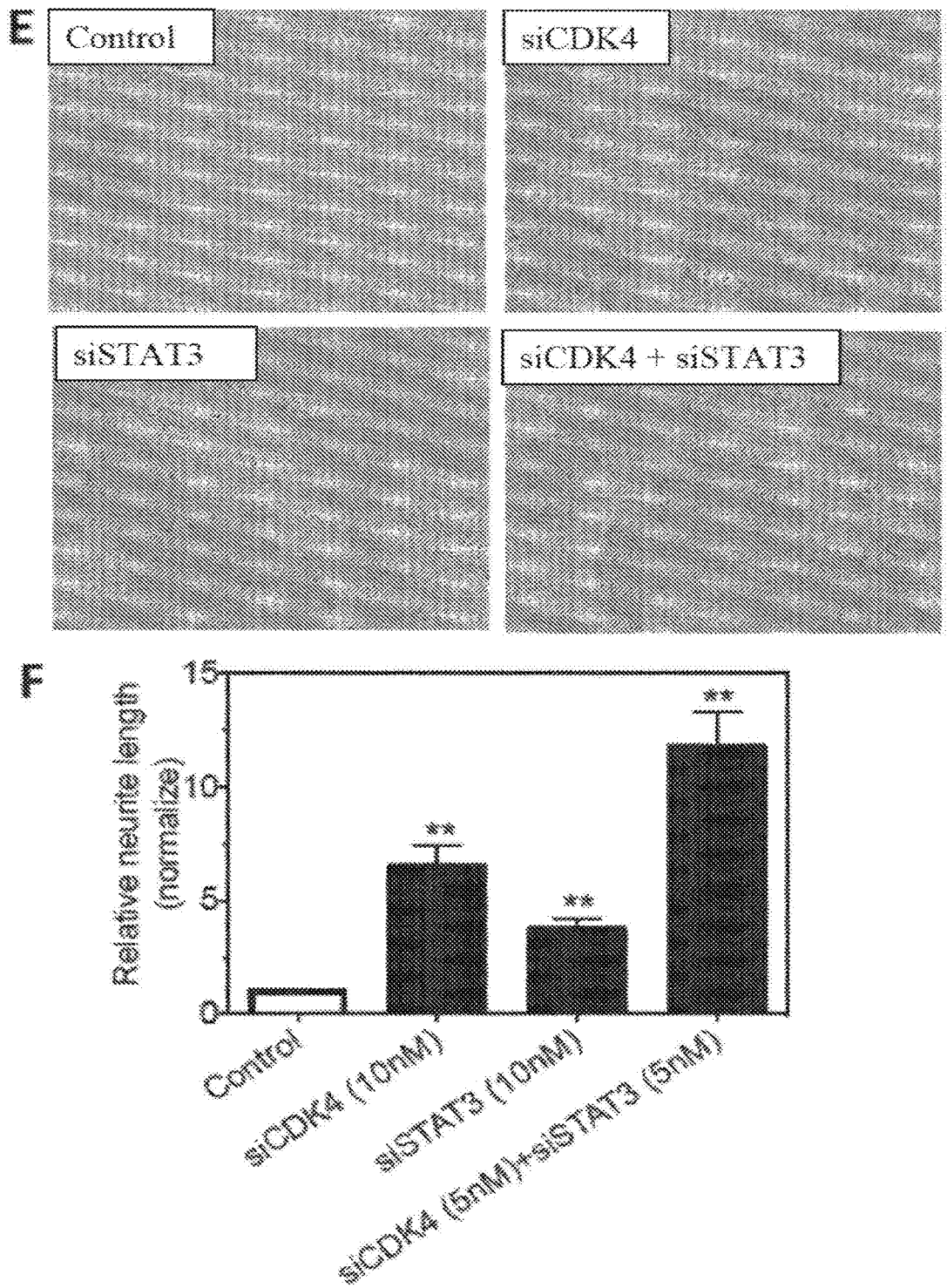

CDK4 and STAT3 Play a Role in Mediating the Differentiation-inducing Function of MIR-506-3P/MIR-124-3P Family. The targets of miR-506-3p/miR-124-3p family were further investigated. Table 2 shows that the expression changes of the 10 predicted target genes of miR-506-3p/miR-124-3p induced by their overexpressions are almost identical (Table 2), further demonstrating that the seed-sequence is dominant in determining the miRNA function. The two miRNAs dramatically down-regulate two of the ten predicted targets, CDK4 and STAT3. FIG. 7A shows the interactions of the two miRNAs with the predicted target sites in the 3'UTR of CDK4 and STAT3. Their target sites were validated in the 3'UTRs of CDK4 and STAT3 using luciferase reporter assays (FIG. 7B-7C). Overexpressions of the two miRNAs were shown to down-regulate endogenous CDK4 and STAT3 protein levels (FIG. 7D). FIG. 7E-7F shows that individual repression of CDK4 and STAT3 expression induces neurite outgrowth, and that their combined repression has an enhanced effect on neurite outgrowth relative to individual repression. These results indicate that CDK4 and STAT3 mediate, at least partially, the differentiation-inducing function of miR-506-3p/miR-124-3p, and suggest that the effect of miR-506-3p/miR-124-3p on cell differentiation are most likely mediated by concordantly down-regulating multiple target genes.

TABLE 2

Changes of expression for the 10 predicted targets of the miR-506-3p/miR-124-3p family induced by miR-506-3p and miR-124-3p overexpression.

| Gene | Gene expression | |
|---|---|---|
| | (1) miR-506-3p | (2) miR-124-3p |
| CDK4 | 0.39 | 0.43 |
| STAT3 | 0.75 | 0.75 |
| CEBPA | 0.88 | 0.86 |
| PML | 1.01 | 1 |
| RARG | 1.02 | 1.03 |
| BDNF | 1.04 | 1.06 |
| THRB | 1.04 | 1.06 |
| RHOQ | 1.07 | 1.13 |
| SHC3 | 1.08 | 1.07 |
| AHR | 1.19 | 1.17 |

Materials. ATRA and cis-RA were from Sigma (St Luis, Mo., USA). Dharmacon miRNA mimic library and individual miRNA mimics were from Thermo Fisher Scientific (Rockford, Ill., USA). miRNA precursors were purchased from Ambion (Foster City, Calif., USA). Rabbit anti-GAP43, anti-NSE, and anti β-TUBULIN III were from Abcam (Cambridge, Mass., USA). Rabbit anti-CALNEXIN, anti-GAPDH and goat anti-rabbit secondary antibody conjugated with horseradish peroxidase (HRP) were from Santa Cruz (Dallas, Tex., USA). Rabbit anti-PARP (cleaved), anti-CASPASE-3, anti-STAT3, and anti-CDK4, were from Cell Signaling (Danvers, Mass., USA). Rabbit anti-Ki67 was from Millipore (Billerica, Mass., USA).

Cell Lines. BE(2)-C cells were purchased from the ATCC. Other cell lines were obtained from the cell line repository at the Greehey Children's Cancer Research Institute. Cells were grown in DMEM/F12 supplemented with 10% fetal bovine serum.

Detection and Quantification of Neurite Outgrowth. Cells were plated and treated in 96-well plates. For detecting neurite outgrowth, cells were placed into ZOOM IncuCyte Imaging System (Essen BioScience) and cell images were taken under 20× microscopic magnification. For detecting neurite outgrowth in a time-dependent manner, cell images were taken every 6 h. The neurite lengths associated with each treatment were calculated using the neurite definition defined for each specific cell line using the NeuroTrack system (Essen BioScience).

Analysis of HCS Data. The relative neurite length associated with cells in each well on the screen plates was determined as above. In order to allow for plate-to-plate comparison, neurite length associated with each well in each plate was first internally normalized to the mean of the corresponding plate, and multiple screen plates were then aggregated together to generate the neurite length distribution. The data were then further analyzed to determine the distribution of the unaffected cells as described below, and to identify differentiation-inducing miRNA mimics.

Kolmogorov-Smirnov Goodness-Of-Fit Test For Gamma Model Validity. In order to examine whether the neurite length distribution of the untreated cells fit Gamma distribution, Gaussian kernel smoothing was first performed to generate the empirical density curve based on the neurite length distribution histogram of the untreated cells, and Gamma model parameters (a, b) were then estimated by minimizing the area in between empirical and Gamma distribution curves. Statistical significance of the fitness to Gamma distribution was examined by Kolmogorov-Smirnov goodness-of-fit test, with $p<0.05$ considered as rejecting the null hypothesis that the neurite length distribution fits Gamma distribution.

Western Blots. Cell lysates were prepared using RIPA buffer. Protein concentration was determined using the Pierce BCA assay (Thermo Fisher Scientific). For electrophoresis, equal amounts of cell lysate were resolved by SDS-PAGE and transferred to Immun-Blot PVDF membranes (Bio-Rad Laboratories). Membranes were blocked and probed with primary antibodies to specific proteins. Bound antibodies were detected with secondary antibodies conjugated with horseradish peroxidase (HRP) visualized by enhanced chemiluminescent (ECL) substrate (Pierce).

Cell Growth Rate Assay. Cells were plated in 96-well plates and were treated with specified conditions. Cell were placed into the IncuCyte imaging system and cell confluence was monitored every 6 h for 120 h. The cell growth curves were derived by comparing the cell confluences at different time points.

Cell Viability Assay. Cells were plated in 96-well format and treated as specified. After culturing for 120 h, cell viability was determined using the CellTiter-Glo Luminescent Cell Viability Assay (Promega).

Colony Formation Assay. Cells were transfected as specified and cultured overnight. 500 cells were re-plated in 10 cm dishes. After 14 days, colonies were visualized by staining with 1% crystal violet. Colony numbers and sizes were analyzed using Image J (NIH, Bethesda, Md.).

Enrichment Analysis Of Mirna Seed Families. We use random permutation to examine whether miRNA seed families are significantly enriched in the identified set of differentiation-inducing miRNAs. The miRNA mimic library includes mimics for 1231 human miRNAs listed in miRBase 16.0. Among these miRNAs, 900 miRNAs have unique seed sequences; 331 miRNAs share seed sequences with at least one other miRNA, constituting 125 seed sequence families. To calculate the probability of miRNAs from the same seed families randomly appears in a set of 14 miRNAs, 14 miRNAs were randomly drawn from the 1231 miRNAs, and the number of non-unique seed sequences within the 14 miRNAs is counted (X). $10^8$ permutations were run to determine the probability that at least X non-unique seed sequences appear in a randomly selected set of 14 miRNAs (p(X)).

Mirna Target Prediction And Pathway Analysis. miRNA target sites in 3'UTRs were predicted based on seed sequence complementarity and were identified using the IPA Pathway analysis function, which identifies any 7-nucleotide region (3'-5') in a given 3' UTR completely complementary to the seed sequence of a miRNA (2nd-8th or 1st-7th nucleotides, 5'-3') as a potential target site of this miRNA. To identify targets that potentially mediate the differentiation-inducing function of our identified miRNAs, we first identified the genes that have been known to relate to neuroblastoma differentiation using IPA. From this gene list, predicted targets were identified for each miRNA and generated the predicted miRNA:target interaction network mediating the differentiation-inducing function of the identified miRNAs.

Mrna And Mirna Expression. Total RNA was isolated as previously described (Du et al., *Mol Cancer Res*, 2009, 7(8):1234-43). mRNA expression profiling was done using the Illumina mRNA WG-6 v3 microarray platform. miRNA expression was measured by qRT-PCR using TaqMan microRNA Assays (Life Technologies) with average expression of RNU44 RNA, RNU19 RNA, GAPDH mRNA and 18s rRNA used as controls for normalizing RNA loading.

Luciferase Reporter Assay. The segments of the wildtype 3' UTRs for CDK4 and STAT3 containing the predicted target sites of miR-506-3p and miR-124-3p were cloned from human genomic DNA. Mutant constructs were generated with the seed target site (GUGCCUU (SEQ ID NO:4)) replaced by CACGGUU (SEQ ID NO:5). The 3' UTRs were cloned downstream of the firefly luciferase coding sequences into the pmirGLO dual-luciferase reporter (Promega), a vector containing both firefly and Renilla luciferase cDNAs under the control of separate promoter/terminator systems. The firefly luciferase was used as the primary reporter for miRNA regulation of the 3' UTR. The Renilla luciferase is an internal control for normalization. BE(2)-C cells were co-transfected with luciferase reporters (0.8 ng/μl) and miRNA mimics or control oligonucleotide (oligo) (25 nM). Luciferase activities were measured after 72 h using the Dual-Glo Luciferase Assay System (Promega). Firefly luciferase activity was normalized to Renilla luciferase activity to evaluate the effect of the miRNAs.

Statistical Analysis. For HCS, p-value for neurite length associated with each miRNA mimic was evaluated by assuming the distribution of neurite lengths follows Gamma distribution, and false Discovery Rate (FDR) was determined by Benjamini-Hochberg correction method for multiple tests (Benjamin, *Journal of the Royal Statistical Society Series B (Methodological)*, 1995, 57(1):12). We consider a miRNA with FDR <0.01 as significantly inducing neurite outgrowth. For all other conditions, the statistical significance for each treatment was determined using t-test by comparing the treatment group with control, with $p<0.05$ considered statistically significant.

I. Nucleic Acids

The present invention concerns miRNAs that can be employed in therapeutic applications, particularly those related to neuroblastoma. The RNA may have been endogenously produced by a cell, or been synthesized or produced chemically or recombinantly. They may be isolated and/or purified. The term "miRNA," unless otherwise indicated, refers to the processed RNA, after it has been cleaved from its precursor.

In certain embodiments, a miRNA is designated with a "5P" or "3P" suffix. "5P" indicates that the mature miRNA derives from the 5' end of the precursor and a corresponding "3P" indicates that it derives from the 3' end of the precursor, as described on the world wide web at sanger.ac.uk.

In some embodiments of the invention, methods and compositions involving miRNA may concern miRNA and/ or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA containing vectors, control nucleic acids, and other probes and primers.

Nucleic acids, and mimetics thereof, of the invention may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, or 25 contiguous nucleotides.

The term "recombinant" may be used and this generally refers to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine. nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3-5 internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3 position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake, and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2' deoxyguanosine nucleotides and nucleic acid analogs thereof).

E. Modified Nucleotides

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments, are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, Biosearch Technologies and NEN. Functional groups may be prepared according to ways known to those of skill in the art, including the representative information found in U.S. Pat. Nos. 4,404,289; 4,405,711; 4,337,063 and 5,268,486, and U.K. Patent 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino) butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

A nucleic acid may be made or prepared by any technique known to one of ordinary skill in the art, such as for example, chemical synthesis, enzymatic production or biological production. It is specifically contemplated that nucleic acids of the invention are chemically synthesized.

F. Labels and Labeling Techniques

In some embodiments, the present invention concerns miRNA that are labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Labels on miRNA or miRNA probes may be colorimetric (includes visible and UV spectrum, including fluorescent), luminescent, enzymatic, or positron emitting (including radioactive). The label may be detected directly or indirectly. Radioactive labels include 125I, 32P, 33P, and 35S. Examples of enzymatic labels include alkaline phosphatase, luciferase, horseradish peroxidase, and β-galactosidase. Labels can also be proteins with luminescent properties, e.g., green fluorescent protein and phicoerythrin.

II. Pharmaceutical Formulations and Administration

In certain embodiments, the invention also provides compositions comprising 1, 2, 3 or more anti-cancer agents with one or more of the following: a pharmaceutically acceptable diluent; a carrier; a solubilizer; an emulsifier; a preservative; and/or an adjuvant. Such compositions may contain an effective amount of at least one anti-cancer agent. Thus, the use of one or more anti-cancer agents that are provided herein in the preparation of a pharmaceutical composition of a medicament is also included. Such compositions can be used in the treatment of neuroblastoma.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, the cancer cell is a tumor cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of the invention include supplying or enhancing the activity of one or more miRNAs in a cell. The present invention also concerns inducing certain cellular characteristics by providing to a cell a particular nucleic acid, such as a specific synthetic miRNA molecule. However, in methods of the invention, the miRNA molecule need not be synthetic. They may have a sequence that is identical to a naturally occurring miRNA or they may not have any design modifications. In certain embodiments, the miRNA molecule is synthetic, as discussed herein.

The particular nucleic acid molecule provided to the cell is understood to correspond to a particular miRNA or seed family in the cell, and thus, the miRNA in the cell is referred to as the "corresponding miRNA." It is contemplated, however, that the miRNA molecule introduced into a cell is not a mature miRNA but is capable of becoming a mature miRNA under the appropriate physiological conditions. In particular embodiments, more than one miRNA molecule is introduced into a cell.

Methods include identifying a cell or patient in need of inducing those cellular characteristics. Also, it will be understood that an amount of a synthetic nucleic acid that is provided to a cell or organism is an "effective amount," which refers to an amount needed to achieve a desired goal, such as inducing a particular cellular characteristic(s).

In certain embodiments of the methods include providing or introducing to a cell a nucleic acid molecule corresponding to a mature miRNA in the cell in an amount effective to achieve a desired physiological result.

Moreover, methods can involve providing synthetic or nonsynthetic miRNA molecules. It is contemplated that in these embodiments, methods may or may not be limited to providing only one or more synthetic miRNA molecules or only one or more nonsynthetic miRNA molecules. Thus, in certain embodiments, methods may involve providing both synthetic and nonsynthetic miRNA molecules. In this situation, a cell or cells are most likely provided a synthetic miRNA molecule corresponding to a particular miRNA and a nonsynthetic miRNA molecule corresponding to a different miRNA.

In some embodiments, there is a method for reducing or inhibiting cell proliferation in a cell comprising introducing into or providing to the cell an effective amount of a synthetic or nonsynthetic miRNA molecule that corresponds to an miRNA sequence.

In particular embodiments, the cancer is neuroblastoma. Methods of the invention can further comprise administering a second therapy, such as chemotherapy, radiotherapy, surgery, or immunotherapy. The nucleic acid can be transcribed from a nucleic acid vector, such as a plasmid vector or a viral vector.

Methods of treating a pre-cancerous or cancerous condition include contacting or administering to a pre-cancerous or cancer cell one or more nucleic acid comprising a miRNA sequence.

In certain aspects, one or more miRNA sequence may include or comprise a modified nucleobase or nucleic acid sequence.

The methods may further comprise administering a second therapy. The second therapy can be, but is not limited to chemotherapy, radiotherapy, surgery, or immunotherapy.

In still further aspects, one or more miRNA are transcribed from a nucleic acid vector, such as a plasmid or viral vector.

In certain aspects, a subject is administered: one or more nucleic acid possessing a function of an miRNA having a nucleic acid segment having at least 80, 85, 90, 95, 97, 98, 99, or 100% nucleic acid sequence identity to those miRNA decreased or down-regulated in a disease or condition to be treated.

Synthetic nucleic acids can be administered to the subject or patient using modes of administration that are well known to those of skill in the art, particularly for therapeutic applications. It is particularly contemplated that a patient is human or any other mammal or animal.

It will be understood in methods of the invention that a cell or other biological matter such as an organism (including patients) can be provided an miRNA or miRNA molecule corresponding to a particular miRNA by administering to the cell or organism a nucleic acid molecule that functions as the corresponding miRNA once inside the cell. The form of the molecule provided to the cell may not be the form that acts as an miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa.

In addition, methods of the invention concern employing one or more nucleic acids corresponding to an miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule. Cancer therapies also include a variety of combination therapies with both chemical and radiation based treatments. Combination chemotherapies include but are not limited to, for example, bevacizumab, cisplatin (CDDP), carboplatin, EGFR inhibitors (gefitinib and cetuximab), procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, etoposide (VP16), tamoxifen, raloxifene, estrogen receptor binding agents, taxol, taxotere, gemcitabien, navelbine, farnesyl-protein transferase inhibitors, transplatinum, 5-fluorouracil, vincristin, vinblastin and methotrexate, or any analog or derivative variant thereof.

The invention claimed is:

1. A synthetic microRNA mimic comprising a double stranded RNA comprising (i) a first RNA component comprising a seed sequence of aaggcac (SEQ ID NO:3) and a mature sequence that is at least 90% identical to uaaggcac-ccuucugaguaga (SEQ ID NO:1), and (ii) a second RNA component comprising a complement of the first RNA component.

2. The synthetic microRNA mimic of claim 1, wherein the mimic is at most 150 nucleotides in length.

3. The synthetic microRNA mimic of claim 1, wherein the mimic is 30 to 130 nucleotides in length.

* * * * *